US008048630B2

(12) United States Patent
Nix et al.

(10) Patent No.: US 8,048,630 B2
(45) Date of Patent: Nov. 1, 2011

(54) METHODS AND AGENTS FOR DETECTING PARECHOVIRUS

(75) Inventors: William Allan Nix, Bethlehem, GA (US); M. Steven Oberste, Alpharetta, GA (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 301 days.

(21) Appl. No.: 12/299,097

(22) PCT Filed: May 1, 2006

(86) PCT No.: PCT/US2006/016624
§ 371 (c)(1),
(2), (4) Date: Oct. 30, 2008

(87) PCT Pub. No.: WO2007/133189
PCT Pub. Date: Nov. 22, 2007

(65) Prior Publication Data
US 2010/0035230 A1    Feb. 11, 2010

(51) Int. Cl.
*C12Q 1/68* (2006.01)
*C07H 21/04* (2006.01)
(52) U.S. Cl. ..................... 435/6.12; 536/24.3
(58) Field of Classification Search ............ None
See application file for complete search history.

(56) References Cited

U.S. PATENT DOCUMENTS

| | | | |
|---|---|---|---|
| 6,846,621 | B1 | 1/2005 | Oberste et al. |
| 7,101,554 | B2 | 9/2006 | Niklasson |
| 2004/0023211 | A1 | 2/2004 | Groen et al. |
| 2004/0253583 | A1 | 12/2004 | Ecker et al. |
| 2004/0265793 | A1 | 12/2004 | Niklasson et al. |
| 2005/0123908 | A1 | 6/2005 | Oberste et al. |
| 2005/0244851 | A1 | 11/2005 | Blume et al. |
| 2007/0134652 | A1 | 6/2007 | Slepnev et al. |

FOREIGN PATENT DOCUMENTS

| | | |
|---|---|---|
| WO | WO 03/019197 A2 | 3/2003 |
| WO | WO 03/091386 A2 | 11/2003 |
| WO | WO 2006/097723 | 9/2006 |
| WO | WO 2007/011210 | 1/2007 |

OTHER PUBLICATIONS

Fuchs & Podda. Encyclopedia of Medical Genomics and Proteomics. Marcel Dekker, New York (2005), pp. 403-404.*
Joki-Korpela et al. Diagnosis and Epidemiology of Echovirus 22 Infections. Clinical Infectious Diseases 26:129-36 (1998).*
Pallansch & Oberste. The Infectious Etiology of Chronic Diseases. The National Acadamies Press, Washington D.C. (2004), pp. 52-59.*
GenBank GI:24898926, Apr. 8, 2004.
GenBank GI:61097777, Mar. 11, 2005.
GenBank GI:323688, Aug. 2, 1993.

GenBank GI:3928983, May 11, 2000.
GenBank GI:21309875, Aug. 9, 2002.
GenBank GI:21309877, Aug. 9, 2002.
GenBank GI:21309879, Aug. 9, 2002.
Abed and Boivin, "Molecular Characterization of a Canadian *Human parechovirus* (HPeV)-3 Isolate and its Relationship to Other HPeVs," *J Med. Virol.* 77:566-570, 2005.
Albert and Fenyö, "Simple, Sensitive, and Specific Detection of Human Immunodeficiency Virus Type 1 in Clinical Specimens by Polymerase Chain Reaction with Nested Primers," *J. Clin. Microbiol.* 28:1560-1564, 1990.
Alho et al., "Diagnostic Potential of *Parechovirus* Capsid Proteins," *J. Clin. Microbiol.* 41:2294-2299, 2003.
Beld et al., "Highly Sensitive Assay for Detection of Enterovirus in Clinical Specimens by Reverse Transcription-PCR with an Armored RNA Internal Control," *J. Clin. Microbiol.* 42:3059-3064, 2004.
Benschop et al., "*Human parechovirus* Infections in Dutch Children and the Association between Serotype and Disease Severity," *Clin. Infect. Dis.* 42:204-210, 2006.
Boivin et al., "*Human parechovirus* 3 and Neonatal Infections," *Emerg. Infect. Diseases 11*; :103-107, 2005.
Corless et al., "Development and Evaluation of a 'Real-Time' RT-PCR for the Detection of *Enterovirus* and *Parechovirus* RNA in CSF and Throat Swab Samples." *J. Med Virol.* 67:555-562, 2002.
Focus Diagnostics Catalog Search, Dec. 20, 2005.
GBMC Healthcare, #S51171: Enterovirus Panel I, CSF [6075], http://www.specialtylabs.com/clients/gbmc/details.asp?id=S51171 &spt=true.
Ginocchio et al., "Development, Technical Performance, and Clinical Evaluation of a NucliSens Basic Kit Application for Detection of *Enterovirus* RNA in Cerebrospinal Fluid," *J. Clin. Microbiol.* 43:2616-2623, 2005.
Ito et al., "Isolation and Identification of Novel *Human parechovirus*," *J. Gen. Virol.* 85:391-398, 2004.
Joki-Korpela and Hyypiä, "*Parechoviruses*, a Novel Group of Human *Picornaviruses*," *Ann. Med.* 33:466-471, 2001.
Jokela et al., "Detection of Human *Picornaviruses* by Multiplex Reverse Transcription-PCR and Liquid Hybridization," *J. Clin. Microbiol.* 43:1239-1245, 2005.
Khetsuriani et al., "Neonatal *Enterovirus* Infections Reported to the National *Enterovirus* Surveillance System in the United States 1983-2003," *Pediatr. Infect. Dis. J.* 25:889-893, 2006.
Mentel et al., "Real-Time PCR to Improve the Diagnosis of Respiratory Syncytial Virus Infection," *J. Med. Microbiol.* 52:893-896, 2003.
Nijhuis et al., "Rapid and Sensitive Routine Detection of All Members of the Genus *Enterovirus* in Different Clinical Specimens by Real-Time PCR," *J. Clin. Microbiol.* 40:3666-3670, 2002.

(Continued)

*Primary Examiner* — Samuel Woolwine
(74) *Attorney, Agent, or Firm* — Klarquist Sparkman, LLP.

(57) ABSTRACT

The present disclosure provides methods that permit detection of all known species of Parechovirus, including Human parechovirus and Ljungan virus (LV). In particular examples the method includes amplifying at least a portion of the 5'NTR of parechovirus nucleic acid molecules obtained from a sample, and detecting the resulting amplicons, but does not require culturing of the virus. The present disclosure also provides methods for determining which particular species or serotype of parechovirus is present in a biological sample. Also provided are oligonucleotide primers and probes that can be used in the disclosed methods.

29 Claims, 4 Drawing Sheets

OTHER PUBLICATIONS

Niklasson et al., "Could Myocarditis, Insulin-Dependent Diabetes *Mellitus*, and Guillain-Barré Syndrome be Caused by One or More Infectious Agents Carried by Rodents?," *Emerg. Infect. Dis.* 4:187-193, 1998.

Niklasson et al., "A New *Picornavirus* Isolated from Bank Voles (*Clethrionomys glareolus*)," *Virol.* 255:86-93, 1999.

Nix et al., "*Human parechovirus* Disease—Colorado, 2005," Poster presented May 2, 2006.

Nix et al., "Detection of All Known *Parechoviruses* by Real-Time PCR," *J. Clin. Microbiol.* 46:2519-2524, 2008.

Nix et al., "Two *Parechovirus* Diagnostic Assays Utilizing Real Time Taqman or Seminested RT-PCR," 21$^{st}$ Annual Clinical Virology Symposium, Clearwater, FL, May 8, 2005.

Nokso-Koivisto et al., "Presence of Specific Viruses in the Middle Ear Fluids and Respiratory Secretions of Young Children with Acute Otitis Media," *J. Med. Virol.* 72:241-248, 2004.

Oberste, "Detection and Identification of Existing and Emerging Human *Picornaviruses*," *Picornavirus* Program, CDC, Jan. 20, 2006, presented at a Centers for Disease Control and Prevention Tech Forum sponsored by the CDC Tech Transfer Office.

Sipp, "Reports of SIDS-Virus Link Greatly Exaggerated, Experts Say," *Nature Med.* 10:1147, 2004.

Stanway and Hyypiä, "Parechoviruses," *J. Virol.* 73:5249-5254, 1999.

Stanway et al., "*Human parechoviruses*—Biology and Clinical Significance," *Rev. Med. Virol.* 10:57-69, 2000.

Stix, "The Universal Biosensor. A Drug Company Tries to Make a Detector that can Find Nearly any Biopathogen," *Sci. Am.* 287:37-39, 2002.

van der Sanden et al., "Prevalence of *Human parechovirus* in the Netherlands in 2000 to 2007," *J. Clin. Microbiol.* 46:2884-2889, 2008.

Welch et al., "Detection of *Enterovirus* Viraemia in Blood Donors." *Vox Sanguinis* 80:211-215, 2001.

Wu et al., "Development of Taqman RT-Nested PCR System for Clinical SARS-CoV Detection," *J. Virol. Methods* 119:17-23, 2004.

\* cited by examiner

SEQUENCE LISTING

<160> NUMBER OF SEQ ID NOS: 16

<210> SEQ ID NO 1
<211> LENGTH: 19
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(19)
<223> OTHER INFORMATION: S is c or g and w is a or t.

<400> SEQUENCE: 1
caswwgcctc tgggsccaa                                                19

<210> SEQ ID NO 2
<211> LENGTH: 21
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(21)
<223> OTHER INFORMATION: y is c or t and w is a or t

<400> SEQUENCE: 2
ggtacctycw gggcatcctt c                                             21

<210> SEQ ID NO 3
<211> LENGTH: 27
<212> TYPE: DNA
<213> ORGANISM: Artificial
<220> FEATURE:
<223> OTHER INFORMATION: probe
<220> FEATURE:
<221> NAME/KEY: misc_feature
<222> LOCATION: (1)..(27)
<223> OTHER INFORMATION: r is a or g, y is c or t, w is a or t.
<220> FEATURE:
<221> NAME/KEY: misc_feature
<222> LOCATION: (1)..(27)
<223> OTHER INFORMATION: 5' end includes a fluorophore (Yakima Yellow)
      and 3' end includes a quencher (Black Hole Quencher).

<400> SEQUENCE: 3
cctrygggta cctycwgggc atccttc                                       27

<210> SEQ ID NO 4
<211> LENGTH: 18
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(18)
<223> OTHER INFORMATION: w is a or t, r is a or g, y is c or t.

<400> SEQUENCE: 4
cccwgrtcag atccayag                                                 18

<210> SEQ ID NO 5
<211> LENGTH: 21
<212> TYPE: DNA
<213> ORGANISM: Artificial
<220> FEATURE:
<223> OTHER INFORMATION: primer

```
<220> FEATURE:
<221> NAME/KEY: misc_feature
<222> LOCATION: (1)..(21)
<223> OTHER INFORMATION: y is c or t, w is a or t.

<400> SEQUENCE: 5
ggtacttycw gggcattctt c                                              21

<210> SEQ ID NO 6
<211> LENGTH: 8
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: r is a or g.

<400> SEQUENCE: 6 aartagtc                                                              8

<210> SEQ ID NO 7
<211> LENGTH: 8
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: r is a or g

<400> SEQUENCE: 7 aartaatc                                                              8

<210> SEQ ID NO 8
<211> LENGTH: 8
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: r is a or g

<400> SEQUENCE: 8 tcrcagtt                                                              8

<210> SEQ ID NO 9
<211> LENGTH: 8
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: r is a or g

<400> SEQUENCE: 9 tcrcaatt                                                              8

<210> SEQ ID NO 10
<211> LENGTH: 8
<212> TYPE: DNA
<213> ORGANISM: Artificial
<220> FEATURE:
<223> OTHER INFORMATION: primer
```

```
<220> FEATURE:
<221> NAME/KEY: misc_feature
<222> LOCATION: (3)..(3)
<223> OTHER INFORMATION: r is a or g

<400> SEQUENCE: 10 atraattt                                                                         8

<210> SEQ ID NO 11
<211> LENGTH: 8
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (3)..(3)
<223> OTHER INFORMATION: r is a or g

<400> SEQUENCE: 11 atraactt                                                                         8

<210> SEQ ID NO 12
<211> LENGTH: 29
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(29)
<223> OTHER INFORMATION: n is a, c, t, or g; h is a, c, or t.

<400> SEQUENCE: 12
gataatactt tgaaatgac nathccnta                                                  29

<210> SEQ ID NO 13
<211> LENGTH: 35
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(35)
<223> OTHER INFORMATION: y is c or t; r is a or g; n is a, c, t, or g.

<400> SEQUENCE: 13
ccaccaaatc taatgccata atgyttrtar aancc                                          35

<210> SEQ ID NO 14
<211> LENGTH: 32
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(32)
<223> OTHER INFORMATION: n is a, c, t, or g; w is a or t; y is c or t.

<400> SEQUENCE: 14
gaatagtagg gtgcagatag ngwcatytgy tc                                             32

<210> SEQ ID NO 15
<211> LENGTH: 27
<212> TYPE: DNA
<213> ORGANISM: Artificial
<220> FEATURE:
<223> OTHER INFORMATION: primer
```

```
<220> FEATURE:
<221> NAME/KEY: misc_feature
<222> LOCATION: (1)..(27)
<223> OTHER INFORMATION: n is a, c, t, or g; m is a or c

<400> SEQUENCE: 15
gtagacaacc tatttggnmg ngcntgg                                           27

<210> SEQ ID NO 16
<211> LENGTH: 27
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (1)..(27)
<223> OTHER INFORMATION: y is c or t; r is a or g; n is a, c, t, or g.

<400> SEQUENCE: 16
tctaatgcca taatgyttrt araancc                                           27
```

METHODS AND AGENTS FOR DETECTING PARECHOVIRUS

CROSS REFERENCE TO RELATED APPLICATION

This is the U.S. National Stage of International Application No. PCT/US2006/016624, filed May 1, 2006, which was published in English under PCT Article 21(2), which is incorporated herein in its entirety.

FIELD

The present disclosure relates to methods of detecting all members of the genus Parechovirus, including Human parechovirus (HPeV) and Ljungan virus (LV), methods of determining which particular species or serotype is present, as well as nucleic acid sequences that can be used for such methods.

BACKGROUND

The genus Parechovirus is one of the newer additions to the Picornaviridae family. Two virus species, Human parechovirus (HPeV) and Ljungan virus (LV), are currently recognized. Three HPeV serotypes have been described. HPeV1 (formerly echovirus 22) and HPeV2 (formerly echovirus 23) were first isolated and described in 1956 (Wigand and Sabin, *Arch. Gesamte Virusforsch.* 11:224-47, 1961), while HPeV3 was isolated in 1999 in Japan (Ito et al., *J. Gen. Virol.* 85:391-8, 2004). The spectrum of clinical disease of the HPeVs mirrors that of the human enteroviruses (EVs) and includes respiratory and gastrointestinal disease, aseptic meningitis, myocarditis, encephalitis, acute flaccid paralysis, and neonatal sepsis (Stanway et al., *Rev. Med. Virol.* 10:57-69, 2000). A WHO study of 581 cases of HPeV1 infection showed 29% of patients had gastrointestinal symptoms, 26% had respiratory symptoms, and 12% had CNS symptoms (Grist and Bell, *Prog. Med. Virol.* 24:114-57, 1978). Two small sero-epidemiologic studies, in Japan and Finland, indicated that children are infected with HPeVs early in life, reaching a high rate of seroprevalence by the time children reach school age (Joki-Korpela and Hyypia, *Clin. Infect. Dis.* 26:129-36, 1998; Takao et al., *Jpn. J. Infect. Dis.* 54:85-7, 2001). The possibility of high levels of infection with HPeVs in children indicates that, like EVs, many HPeV infections are probably asymptomatic or result in only mild illness.

The Ljungan viruses (LV) were first isolated from bank voles (*Clethrionomys glareolus*) in Sweden in the mid-1990s (Niklasson et al., *Virol.* 255:86-93, 1999). Molecular and physical characterization identified LV as a novel parechovirus, related to, but distinct from, the human parechoviruses. Sequence comparisons of the polymerase gene (3D) of the Swedish LVs with 3D sequences of two previously unclassified North American viruses showed that the two American viruses are LVs (Johansson et al., *J. Gen. Virol.* 84:837-44, 2003). Strain NY64-7855 was isolated in 1964 during an arbovirus survey in St. Lawrence, N.Y. from the red-backed mouse (*C. gapperi*). This virus was later shown to be immunologically related to a virus, OR62-M1146, isolated from *Mictrotus montanus* in Klamath County, Oreg. in 1962, OR62-M 1146. Genomic sequencing of several of the LVs demonstrated that LVs are most closely related to, but distinct from, the HPeVs (Johansson et al., *J. Virol.* 76:8920-30, 2002). It has been demonstrated that up to one-third of captured bank voles develop type I diabetes, and that diabetes in voles is caused by LV (Niklasson et al., *Int. J. Exp. Diab. Res.* 4:1-10, 2003). It has been indicated that LV may be involved in the etiology of a variety of human diseases, including type 1 diabetes mellitus, myocarditis, and Guillain-Barre syndrome, because the incidence of these diseases in northern Sweden rises and falls in parallel with the cyclic population changes observed in the small rodent species from which LV has been isolated (Niklasson et al., *Emerg. Infect. Dis.* 4:187-93, 1998). The possibility of a zoonotic relationship between LV infection and human disease remains under investigation, with no definitive association has been found to date.

Current methods of detecting Parechovirus amplify and detect Parechovirus nucleic acids, since no antibodies to the virus are yet available (see for example the methods described in Benschop et al., *Clin. Infect. Dis.* 42:204-10, 2006, Oberste et al., *J. Med. Virol.* 58:178-81, 1999; Read et al., *J. Clin. Microbiol.* 35:691-6, 1997; Shimizu et al., *Pediatr. Infect. Dis.* 14:584-8, 1995; Legay et al., *J. Virol. Meth.* 102:157-60, 2002; Corless et al., *J. Med. Virol.* 67:555-62, 2002; Jokela et al., *J. Clin. Microbiol.* 43:1239-45, 2005; Joki-Korpela and Hyypia, *Clin. Infect. Dis.* 26:129-36, 1998). However, the current methods do not permit detection of all known members of the Parechovirus genus in a single assay.

Benschop et al. (*Clin. Infect. Dis.* 42:204-10, 2006) disclose a method that permits detection of HPeV1, HPeV2, and HPeV3, but not LV. Corless et al. (*J. Med. Virol.* 67:555-62, 2002) disclose a method that permits detection of HPeV1 and HPeV2, but not HPeV3 or LV. Jokela et al. (*J. Clin. Microbiol.* 43:1239-45, 2005) disclose a method that permits detection of HPeV1, HPeV2, and HPeV3, but not LV. Joki-Korpela and Hyypia (*Clin. Infect. Dis.* 26:129-36, 1998) disclose a method that permits detection of HPeV1, but not HPeV2, HPeV3, or LV. Legay et al. (*J. Virol. Meth.* 102:157-60, 2002) disclose a method that permits detection of HPeV1, but not HPeV2, HPeV3, or LV. Oberste et al. (*J. Med. Virol.* 58:178-81, 1999) disclose a method that permits detection of HPeV1, HPeV2, and HPeV3, but not LV. That is, multiple primer sets are used to screen for the presence of all known Parechovirus species using the previously disclosed methods.

In addition, current methods of detecting parechoviruses require culturing of the virus, for example in Vero or rhesus monkey kidney cells. Because this culturing requires several days, methods that include a culturing step do not permit the rapid detection of Parechovirus; furthermore, cell culture isolation is less sensitive than PCR For example, HPeV1 and HPeV2 can be identified by neutralization assay following virus isolation in cell culture, using the available Lim and Benyesh-Melnick antiserum pools (*J. Immunol.* 84:309-17, 1960), using pools E and H (HPeV1), or G and H (HPeV2. However, culturing is required prior to identification, and antigenic typing reagents are not available for HPeV and LV.

Although there are PCR assays based on the 5'UTR region (for example see Nijhuis et al., *J. Clin. Microbiol.* 40:3666-70, 2002) or the VP region (U.S. Pat. No. 6,846,621 to Oberste et al.) of enterovirus, another member of the Picornaviridae family, these assays do not detect HPeV nor LV. In addition, the RT-PCR assays for HPeV are not routinely used to detect HPeV in clinical samples because most lack the required analytical sensitivity to detect viral RNA in original clinical specimens (Benschop et al., *Clin. Infect. Dis.* 42:204-10, 2006; Oberste et al., *J. Med. Virol.* 58:178-81, 1999; Read et al., *J. Clin. Microbiol.* 35:691-6, 1997; Shimizu et al., *Pediatr. Infect. Dis.* 14:584-8, 1995; Legay et al., *J. Virol. Meth.* 102:157-60, 2002; Corless et al., *J. Med. Virol.* 67:555-62, 2002; Jokela et al., *J. Clin. Microbiol.* 43:1239-45, 2005; Joki-Korpela and Hyypia, *Clin. Infect. Dis.* 26:129-36, 1998).

Therefore, methods are needed that permit detection of all known species Parechovirus directly from clinical specimens, for example without the need for culturing the virus.

SUMMARY

The present application relates to methods of detecting all known species of Parechovirus, as well as nucleic acid molecules and kits that can be used in such methods. In particular examples, the method also includes identification of the species (or the serotype) of detected parechovirus. Although there are currently available PCR methods that can detect Human parechovirus (HPeV) (such as serotypes HPeV1, HPeV2, and HPeV3), none of the methods can detect Ljungan virus (LV). The methods described herein are capable of detecting all of the known parechoviruses, including HPeV and LV, and it is proposed that the disclosed primers and probes can amplify and detect yet-to-be-described species of the Parechovirus genus. Furthermore, in some examples the disclosed methods of detecting parechovirus are approximately 10 to 100 times more sensitive than methods that use virus isolation in cell culture. For example, in some examples the reverse transcriptase semi-nested polymerase chain reaction (RT-snpCR) method can detect as little as 1 copy of the parechovirus genome.

Disclosed herein are methods for detecting any Parechovirus species, such as HPeV (including the serotypes HPeV1, HPeV2, HPeV3), and LV. In some examples, the method does not include culturing parechovirus in culture (for example in Vero or rhesus monkey kidney cells) prior to isolating RNA from the sample. Elimination of this step in some examples reduces the cost of the assay, reduces the amount of time that it takes to obtain a test result, or both. In particular examples, the disclosed methods can be used to determine whether a biological sample is infected with parechovirus in less than 24 hours, such as 3-24 hours, 3-16 hours, 4-16 hours, 4-13 hours, for example about 4 hours (for example using 5'-NTR Taqman RT-PCR), about 7 hours (for example using 5'-NTR RT-snPCR), or about 13 hours (for example for using VP1 RT-snPCR).

In particular examples the method includes contacting cDNA reverse transcribed from RNA isolated from a sample with a composition that permits amplification of the cDNA. The method can include extraction of RNA from the sample, reverse transcribing the RNA to cDNA, or both; however, it is possible that one or more of such steps have already been performed. In some examples, a single reaction vessel is used to both reverse transcribe RNA to cDNA, and amplify the cDNA. The composition used to amplify the cDNA includes a forward primer (such as SEQ ID NO: 1) and a first reverse primer (such as SEQ ID NO: 4), wherein the forward and first reverse primers are complementary to opposite strands of a parechovirus 5' non-translated region (5'NTR), thereby permitting the primers to hybridize to a region of the 5'NTR.

An amplification procedure is performed under conditions sufficient to amplify parechovirus cDNA and produce parechovirus amplicons from any Parechovirus species, wherein the amplicon includes at least a portion of the parechovirus 5'NTR nucleic acid sequence if parechovirus is present in the sample. Methods of amplification of nucleic acid molecules are known in the art, and include polymerase chain reaction (PCR), such as real time PCR. In some examples, at least two separate PCR reactions are performed.

In some examples, a second amplification procedure is performed after the first amplification procedure, for example to further increase the number of amplicons. In a particular example, the second amplification procedure is performed using semi-nested PCR. For example, at least a portion of the first reaction sample containing amplification products from the first amplification reaction is incubated under conditions sufficient to amplify parechovirus cDNA and produce a parechovirus amplicon from any Parechovirus species, wherein the composition includes the forward primer (such as SEQ ID NO: 1) and a second reverse primer (such as SEQ ID NO: 2), wherein the second reverse primer hybridizes to the parechovirus 5'NTR upstream of where the first reverse primer hybridizes to the parechovirus 5'NTR.

In some examples, the composition used to amplify the cDNA also includes a probe that includes a detectable label, such has a fluorophore. In particular examples, the probe also includes a quencher molecule. The probe is complementary to a region of the parechovirus 5'NTR nucleic acid sequence, such as a region located between the forward and first reverse primers. An exemplary probe sequence is provided in SEQ ID NO: 3.

The method also includes determining whether parechovirus amplicons are present, wherein the presence of amplicons indicates that at least one Parechovirus species is present in the sample and wherein the absence of amplicons indicates that the sample does not contain parechovirus. Such a determination can be made during the amplification (for example using real time PCR) or following amplification (for example analyzing the amplicons using gel electrophoresis). In some examples the method further includes quantitating the amplicons, for example by using real time quantitative PCR.

Methods of detecting amplicons are known in the art. For example, if the amplification composition includes a probe with a detectable label, detection can include detection of the label, such as detecting fluorescence. In other examples, detection can include analyzing amplicons using gel electrophoresis and visualization of amplicons contained in a resulting gel, size separation matrix, capillary electrophoresis and detection of the emerging amplicon, probing for the presence of the parechovirus amplicon using a probe, or sequencing the parechovirus amplicon. However, one skilled in the art will appreciate that other methods can be used.

Also provided by the present disclosure are methods of determining which particular Parechovirus species (such as HPeV or LV), as well as which serotype (such as HPeV1, HPeV2, or HPeV3) is present in a biological sample. Such methods can be used in combination with the methods described above. For example, if parechovirus amplicons are detected using the methods discussed above, the particular species of Parechovirus present in the sample can be subsequently determined. However, one skilled in the art will appreciate that the methods disclosed for determining which particular Parechovirus species is present can be performed independently of the methods used to determine generally if parechovirus is present in the sample.

For example, the method of determining which particular Parechovirus species is present in a sample can include sequencing at least a portion of the viral protein 1 (VP1) gene of parechovirus, and then determining which Parechovirus species it corresponds to (for example by comparing the sequence to a database, such as EMBL, GenBank, or other database of serotype reference strains). In particular examples, if two nucleotide sequences are greater than 75% identical or have greater than 85% amino acid identity, they are the same type. For example, if the nucleotide sequence of the amplicon has 76% identity to HPeV1, then it is concluded that the sample (and the subject from whom the sample was obtained) is infected with HPeV1. In particular examples, if two nucleotide sequences are less than 70% identical, this indicates that the species is a "new" or previously unidentified (or unsequenced) Parechovirus species. In particular examples, if two nucleotide sequences are 70-75% identical, the result is indeterminant.

In particular examples, the method of determining which Parechovirus species is present in the sample includes contacting cDNA reverse transcribed from RNA isolated from a sample with a composition that permits amplification of the cDNA. Exemplary primers that can be used to reverse transcribe RNA to cDNA for are shown in SEQ ID NOS: 6-11. The composition in which the amplification is performed can include a forward primer (such as SEQ ID NO: 12) and a reverse primer (such as SEQ ID NO: 13), wherein the primers hybridize to opposite strands of a parechovirus nucleic acid sequence; the forward primer to a VP3 sequence and the reverse primer to a 2A sequence. In particular examples, the amplification procedure is performed under conditions sufficient to amplify parechovirus cDNA and produce a parechovirus amplicon that includes at least a portion of the parechovirus VP1 nucleic acid sequence from any Parechovirus species. If desired, at least a portion of this amplification reaction can be further amplified, for example using semi-nested PCR (for example using SEQ ID NOS: 12 and 14 or SEQ ID NOS: 15 and 16) or nested PCR (for example using SEQ ID NOS: 14 and 15). The resulting amplicons can be sequenced using methods known in the art.

Also provided by the present disclosure are isolated nucleic acid molecules, such as probes and primers. For example, disclosed are isolated nucleic acid molecules that consist of SEQ ID NOS: 1-4, or 6-16; nucleic acid molecules that include at least 95% sequence identity to SEQ ID NO: 2 and retains the ability to hybridize to a parechovirus 5'NTR sequence under high or very high stringency conditions; and nucleic acid molecules that include SEQ ID NO: 2 or any of SEQ ID NOS: 6-16.

Kits that include one or more of the disclosed probes or primers are also encompassed by this disclosure. In a particular example, the kit includes 2, 3, 4, 5, 6, 7, 8, 9, 10, 11, 12, 13, 14, or 15 of the disclosed nucleic acid molecules. In some examples, the kit can include one or more agents used to reverse transcribe RNA to cDNA, one or more agents for amplification of cDNA, or combinations thereof.

SEQUENCE LISTING

The nucleotide sequences of the nucleic acids described herein are shown using standard letter abbreviations for nucleotide bases. Only one strand of each nucleic acid sequence is shown, but the complementary strand is understood as included by any reference to the displayed strand. Standard IUB nucleotide ambiguity codes are used: R=A or G; S=C or G, N=G, A, T or C; Y=C or T; W=A or T; M=A or C; and H=A, C, or T.

SEQ ID NO: 1 is the nucleic acid sequence of an exemplary forward primer that can be used to amplify parechovirus cDNA using PCR.

SEQ ID NO: 2 is the nucleic acid sequence of an exemplary semi-nested reverse primer that can be used to amplify parechovirus cDNA using seminested PCR (for example in combination with SEQ ID NO: 1).

SEQ ID NO: 3 is the nucleic acid sequence of an exemplary probe that can be used to detect parechovirus cDNA using real time PCR. In particular examples the 5' end includes a reporter fluorophore (such as Yakima Yellow) and the 3' end includes a quencher (such as Black Hole Quencher@).

SEQ ID NO: 4 is the nucleic acid sequence of an exemplary reverse primer that can be used to amplify parechovirus cDNA using PCR.

SEQ ID NO: 5 is the reverse complement of SEQ ID NO: 2.

Figure 4:
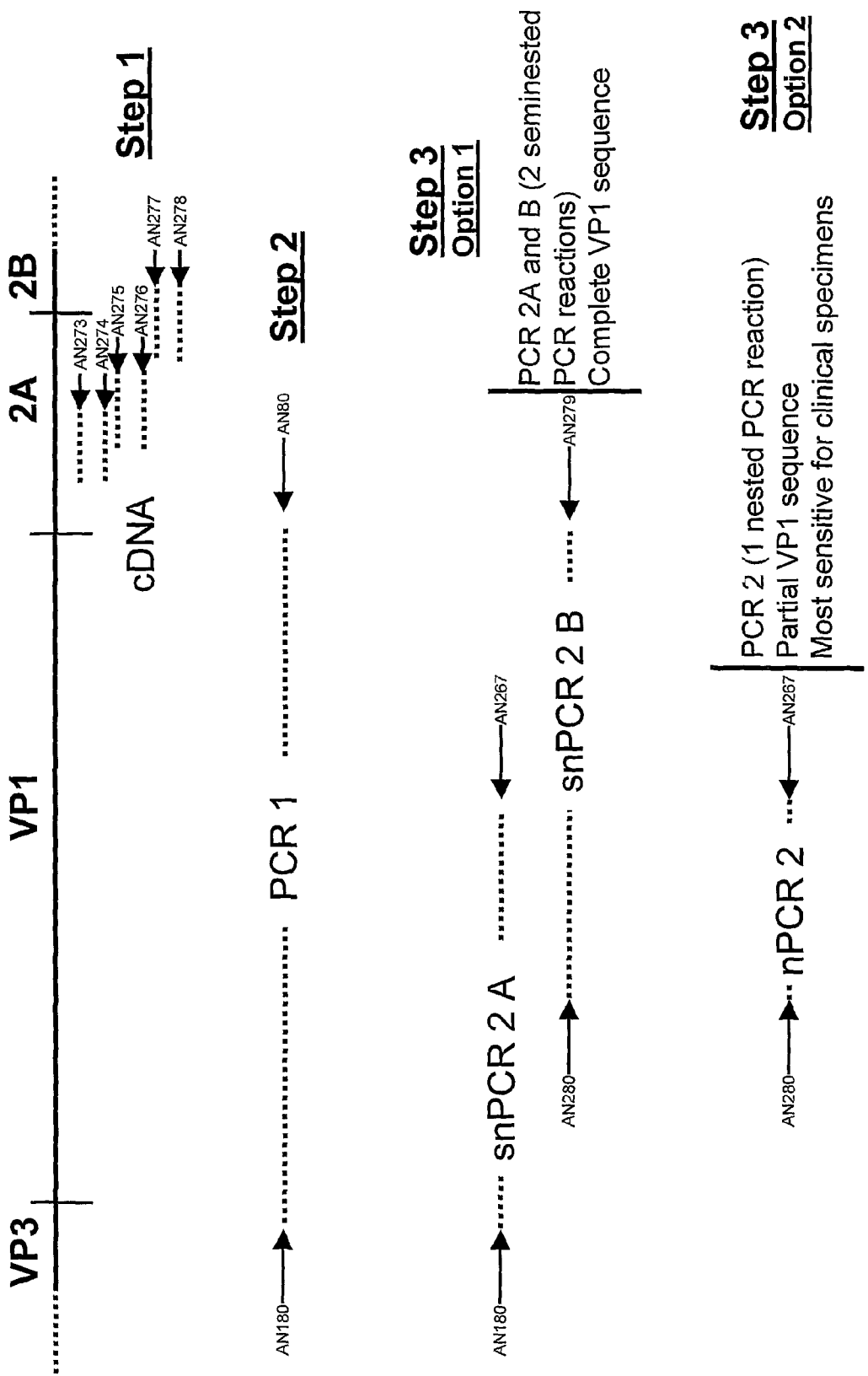
FIG. 4 is a schematic drawing showing the strategy used for determining which Parechovirus species is present (not to scale).

SEQ ID NOS: 6-11 (AN273, AN274, AN275, AN276, AN277, and AN278, respectively) are the nucleic acid sequences of primers that can be used to reverse transcribe RNA to DNA from a 2A region (SEQ ID NOS: 6-9) or 2B region (SEQ ID NOS: 10-11) of parechovirus (see FIG. 4).

SEQ ID NOS: 12-16 (AN180, AN80, AN267, AN280, and AN279 respectively) are nucleic acid sequences of primers that can be used to amplify a VP1 region (or portion thereof) of parechovirus (see FIG. 4).

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a parechovirus amplicon" includes single or plural amplicons and is considered equivalent to the phrase "comprising at least one parechovirus amplicon." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

5' NTR: 5' non-translated region
BHQ: Black Hole Quencher®
CCID50: 50% cell culture infectious dose
CSF: cerebrospinal fluid
HPeV: human parechovirus
LV: Ljungan virus
PCR: polymerase chain reaction
RT-snPCR: reverse transcription-semi-nested PCR
VP1: viral protein 1

5' non-translated region (5'NTR): The regions of a cDNA 5' to the initiation (AUG) site which are not translated to make a peptide.

Amplifying a nucleic acid molecule: To increase the number of copies of a nucleic acid molecule, for example using PCR. The resulting amplification products are called "amplicons."

An example of in vitro amplification is the polymerase chain reaction (PCR), in which a nucleic acid molecule, such as cDNA reverse transcribed from RNA extracted from a biological sample obtained from a subject, is contacted with a pair of oligonucleotide primers, under conditions that allow for hybridization of the primers to the nucleic acid molecule (such as parechoviral cDNA). The primers are extended under suitable conditions, dissociated from the template, and then re-annealed, extended, and dissociated to amplify the number of copies of the nucleic acid molecule. Other examples of ill vitro amplification techniques include real-time PCR, quantitative real-time PCR, reverse transcriptase semi-nested PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Complementary: Complementary binding occurs when the base of one nucleic acid molecule forms a hydrogen bond to the base of another nucleic acid molecule. For example, complementary binding normally occurs between a probe or primer (such as any of SEQ ID NOS: 1-4) to a parechovirus 5'NTR nucleic acid molecule. However, nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Detect: To determine the existence or presence of, for example to determine whether a nucleic acid molecule is present in a sample or to determine if an amplicon is present following amplification. For example, detection can include determining whether parechoviral RNA is present in a sample, or whether parechoviral amplicons are present during or following an amplification reaction.

Fluorophore: A chemical compound, which when excited by exposure to a particular stimulus such as a defined wavelength of light, emits light (fluoresces), for example at a different wavelength.

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules eliminates the need for an external source of electromagnetic radiation, such as a laser. Examples of chemiluminescent molecules include, but are not limited to, aequorin.

Examples of particular fluorophores that can be used in the probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, Yakima Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron.®. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other fluorophores known to those skilled in the art can also be used, for example those available from Molecular Probes (Eugene, Oreg.).

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid molecules. Generally, the temperature of hybridization and the ionic strength (such as the $Na^+$ concentration) of the hybridization buffer will determine the stringency of hybridization. However, for hybridization conditions related to PCR, the salt concentration is generally fixed by the buffer conditions and stringency of hybridization controlled by temperature (for example 42° C. low stringency, 48-50° C. medium stringency, and 55-60° C. high stringency).

Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). For purposes of this disclosure, "stringent conditions" encompass conditions under which hybridization only will occur if there is less than 25% mismatch between the hybridization molecule and the target sequence. "Moderate stringency" conditions are those under which molecules with more than 25% sequence mismatch will not hybridize; conditions of "medium stringency" are those under which molecules with more than 15% mismatch will not hybridize, and conditions of "high stringency" are those under which sequences with more than 10% mismatch will not hybridize. Conditions of "very high stringency" are those under which sequences with more than 5% mismatch will not hybridize.

Moderately stringent hybridization conditions are when the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 55° C. with a wash solution containing 0.2×SSC and 0.1% sodium dodecyl sulfate.

Very highly stringent hybridization conditions are when the hybridization is performed at about 42° C. in a hybridization solution containing 25 mM $KPO_4$ (pH 7.4), 5×SSC, 5×Denhart's solution, 50 µg/mL denatured, sonicated salmon sperm DNA, 50% formamide, 10% Dextran sulfate, and 1-15 ng/mL probe (about $5 \times 10^7$ cpm/µg), while the washes are performed at about 65° C. with a wash solution containing 0.2×SSC and 0.1% sodium dodecyl sulfate. 20×SSC is 3.0 M NaCl/0.3 M trisodium citrate.

Isolated: An "isolated" biological component (such as a nucleic acid molecule, for example RNA) has been substantially separated, produced apart from, or purified away from other biological components. Nucleic acid molecules which have been "isolated" include nucleic acids molecules purified by standard purification methods (for example RNA extracted from a clinical sample), as well as those chemically synthesized. Isolated does not require absolute purity, and can include nucleic acid molecules that are at least 50% isolated, such as at least 75%, 80%, 90%, 95%, 98%, 99% or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part of. Examples of labels include, but are not limited to, radioactive isotopes, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Nucleic acid molecule (or sequence): A deoxyribonucleotide or ribonucleotide polymer including without limitation, cDNA, mRNA, genomic DNA, and synthetic (such as chemically synthesized) DNA or RNA. The nucleic acid molecule can be double stranded (ds) or single stranded (ss). Where single stranded, the nucleic acid molecule can be the sense strand or the antisense strand. Nucleic acid molecules can include natural nucleotides (such as A, T/U, C, and G), and can also include analogs of natural nucleotides.

Nucleotide: The fundamental unit of nucleic acid molecules. Includes, but is not limited to, a monomer that includes a base, such as a pyrimidine, purine, or synthetic analogs thereof, linked to a sugar and one or more phosphate groups. A set of bases linked to a peptide backbone, as in a peptide nucleic acid (PNA), can be used as a substitute for a nucleic acid molecule. A nucleotide is one monomer in a polynucleotide. A nucleotide sequence refers to the sequence of bases in an oligonucleotide.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). However, nucleotides can include those nucleotides containing modified bases, modified sugar moieties and modified phosphate backbones, for example as described in U.S. Pat. No. 5,866,336 to Nazarenko et al.

Oligonucleotide: A linear polynucleotide (such as DNA or RNA) sequence, for example of at least 6 nucleotides, for example at least 9, at least 15, at least 18, at least 24, at least 30, at least 50, at least 100, at least 200 or even at least 500 nucleotides long. An oligonueleotide can contain non-naturally occurring portions, such as altered sugar moieties or inter-sugar linkages, such as a phosphorothioate oligodeoxynucleotide. In particular examples, an oligonucleotide containing non-naturally occurring portions can bind to RNA or DNA, and include peptide nucleic acid (PNA) molecules.

Parechovirus: A member of the Picornaviridae family, which includes two virus species, Human parechovirus (HPeV) and Ljungan virus (LV). Parechovirus, like other members of Picornaviridae, is a small, non-enveloped, single-stranded RNA virus. Three HPeV serotypes have been described. HPeV1 (formerly echovirus 22), HPeV2 (formerly echovirus 23), and HPeV3. Symptoms of HPeV infection include respiratory and gastrointestinal disease, aseptic meningitis, myocarditis, encephalitis, acute flaccid paralysis, neonatal sepsis, and combinations thereof. Diabetes has been associated with LV infection in rodents.

Polymerase chain reaction (PCR): A method whereby a limited segment of a nucleic acid molecule, such as a targeted segment, is amplified repetitively to produce a large amount of DNA molecules consisting of only that segment. The procedure depends on repetition of a large number of priming and transcription cycles. In each cycle, two oligonucleotide primers bind to the segment, and define the limits of the segment. A primer-dependent DNA polymerase then transcribes, or replicates, the strands to which the primers have bound. Thus, in each cycle, the number of DNA duplexes is doubled. The resulting PCR products are called amplicons. In a particular example, the methods disclosed herein include the step of PCR amplifying a portion of the 5'NTR of *parechovirus*.

Primer: A short nucleic acid molecule which can be used to initiate the synthesis of a longer nucleic acid sequence. In one example, a primer includes a detectable label, and is referred to as a probe.

Primers can be annealed to a complementary target DNA strand (such as a parechovirus 5'NTR cDNA) by nucleic acid hybridization to form a hybrid between the primer and the target DNA strand, and then the primer extended along the target DNA strand by a DNA polymerase enzyme. Primer pairs can be used for amplification of a nucleic acid sequence, for example by PCR or other nucleic-acid amplification methods.

In particular examples, a primer is about 6-50 nucleotides, for example about 10-50 nucleotides, 15-40 nucleotides, or 15-30 nucleotides.

Quantitating a nucleic acid molecule: Determining or measuring a quantity (such as a relative quantity) of nucleic acid molecule present, such as the number of amplicons or the number of nucleic acid molecules present in a sample. In particular examples, it is determining the relative amount or actual number of nucleic acid molecules present in a sample, such as the number of parechovirus RNA or cDNA molecules present or the number of parechovirus amplicons present.

Quenching of fluorescence: A reduction of fluorescence. In some examples, quenching of a fluorophore's fluorescence on a probe occurs when a quencher molecule (such as a Black Hole Quencher®, Biosearch Technologies) is present in sufficient proximity to the fluorophore that it reduces the fluorescence signal of the probe when the probe is intact, but not when the probe is cleaved.

Real-time PCR: A method for detecting and measuring products generated during each cycle of a PCR, which are proportionate to the amount of template nucleic acid (such as parechovirus nucleic acid) prior to the start of PCR. The information obtained, such as an amplification curve, can in some examples be used to quantitate the initial amounts of template nucleic acid sequence.

Reverse transcription (RT): A procedure catalyzed by reverse transcriptase that synthesizes a cDNA from a single stranded RNA molecule, with the use of oligonucleotide primers having free 3'-hydroxyl groups. In particular examples, RNA isolated from a sample is subjected to RT to generate cDNA, which is amplified.

Sample: Biological specimens, such as those obtained from a subject that contains nucleic acid molecules (for example DNA, cDNA, RNA, mRNA, or combinations thereof). In one example, a sample is one in which parechovirus would be found if the subject from which the sample were obtained was infected with parechovirus. In particular examples, a sample is obtained from a subject suspected of suffering from a disease or syndrome that is at least partially caused by a parechovirus. The subject may also be an asymptomatic individual considered to be at risk of parechovirus infection. In a particular example, the sample is obtained from a human subject or a non-human mammalian subject.

The sample can be a cellular sample such as a tissue sample, for example a tissue biopsy, surgical specimen, fine needle aspirate, amniocentesis sample or autopsy material (such as a sample of lung or spleen tissue obtained as a biopsy or post-mortem); a fluid sample such as blood (or a portion thereof, such as plasma or serum), saliva, sputum, urine, cerebrospinal fluid (CSF); a swabbed sample obtained by swabbing a mucus membrane surface such as a nasal surface, a pharyngeal surface, a buccal surface, and the like; an excretion such as feces (for example a stool sample); as well as a sample obtained from other bodily tissues or body fluids commonly used in clinical diagnostic testing.

Sensitivity: The probability that a statistical test will be positive for a true statistic, such as the ability to detect a target nucleic acid molecule if the target nucleic acid molecule is present. Can be calculated by dividing the number of test positive results divided by the number of total test positive and false negative results, and is usually expressed as a percentage.

For example, the sensitivity of the methods disclosed herein is an indication that the methods can detect all known members of the Parechovirus genus, if parechovirus is present. In one example, the sensitivity of the disclosed methods is at least 95%, such as at least 98%, at least 99%, or at least 100%, meaning that at least 95 times out of 100 times the method is performed, the method will detect the presence of parechovirus nucleic acids if they are present in a sample.

Sequence identity: The identity between two or more nucleic acid sequences, or two or more amino acid sequences, is expressed in terms of the identity between the sequences. Sequence identity can be measured in terms of percentage identity; the higher the percentage, the more identical the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biomedical Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (such as C:\seq1.txt); -j is set to a file containing the second nucleic acid sequence to be compared (such as C:\seq2.txt); -p is set to blastn; -o is set to any desired file name (such as C:\output.txt); -q is set to -1; -r is set to 2; and all other options are left at their default setting. For example, the following command can be used to generate an output file containing a comparison between two sequences: C:\Bl2seq-i c:\seq1.txt-j c:\seq2.txt -p blastn -o c:\output.txt -q -1 -r2.

Once aligned, the number of matches is determined by counting the number of positions where an identical nucleotide is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 19 matches when aligned with a test sequence having 20 nucleotides is 95.0 percent identical to the test sequence (19÷20*100=95.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing 21 nucleotides that aligns with 19 consecutive nucleotides from an identified sequence as follows contains a region that shares 90 percent sequence identity to that identified sequence (that is, 19÷21*100=90).

```
   Target Sequence: GGTACCTYCWGGGCATCCTTC (SEQ ID NO: 2)
                    |||||  ||||||||||| ||||
Identified Sequence: GGTACTTYCWGGGCATTCTTC (SEQ ID NO: 5)
```

One indication that two nucleic acid molecules are closely related is that the two molecules hybridize to each other under stringent conditions (such as high or very high stringency), as described above. In some examples, the primers and probes disclosed in SEQ ID NOS: 1-4 can be altered in a few nucleotides (such as 1-2 nucleotides) without affecting the ability of the probe or primer to function properly using the methods disclosed herein. In one example, a probe or primer having at least 80% sequence identity, such as at least 85% sequence identity, at least 90% sequence identity, or even at least 95% sequence identity, can be used in the methods disclosed herein.

Signal: A detectable change or impulse in a physical property that provides information. In the context of the disclosed methods, examples include electromagnetic signals such as light, for example light of a particular quantity or wavelength. In certain examples the signal is the disappearance of a physical event, such as quenching of light. In one example, a label emits a signal capable of detection, such as a fluorescent signal.

Specificity: The probability that a statistical test will be negative for a negative statistic, such as the ability to not produce a positive result if the target nucleic acid molecule is not present. Can be calculated by dividing the number of true negative results by the number total of true negative and false-positive results, and is usually expressed as a percentage.

For example, the specificity of the methods disclosed herein is an indication that the methods can detect all known members of the Parechovirus genus, while not indicating a positive result if parechovirus is absent (for example if another member of Picornaviridae is present, such as an enterovirus). In one example, the specificity of the disclosed methods is at least 95%, such as at least 98%, at least 99%, or at least 100%, meaning that at least 95 times out of 100 times the method is performed, the method will detect the presence of parechovirus nucleic acids if they are present in a sample, and not indicate a positive result if parechovirus is not present.

Subject: Living multi-cellular vertebrate organisms, a category that includes human and non-human mammals, such as veterinary subjects (such as laboratory animals, for example mice, rats, rabbits, or non-human primates). In a particular example, a subject is one that has or is susceptible to infection with a parechovirus.

Target nucleic acid molecule (or sequence): A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid in a sample (such as parechoviral nucleic acids, such as parechoviral RNA), the amplification of which is intended. Purification or isolation of the target nucleic acid molecule, if needed, can be conducted by methods known to those in the art. For example, isolation can be achieved by using a commercially available purification kit or the like. Exemplary target nucleic acid molecules include at least a portion of parechovirus VP1, at least a portion of parechovirus 5'NTR, or combinations thereof.

Under conditions sufficient for: A phrase that is used to describe any environment that permits the desired activity. An example includes contacting cDNA reverse transcribed from RNA extracted from a sample with reagents and temperature conditions sufficient to allow amplification of the cDNA.

Viral protein 1 (VP1) region of parechovirus: Region of the *parechovirus* genome that encodes the protein called VP1, also known as 1D when referring to either the VP1 protein or VP1-encoding genome region. VP1 is one of three proteins that compose the picornavirus virion (virus particle), the others being VP0 and VP3, and there being 60 molecules of each protein present in each virion, organized as 20 subunits (protomers) of roughly triangular shape, each containing one molecule each of VP0, VP3, and VP1. The 20 subunits are arranged in such a way to form a virion whose shape resembles a regular icosahedron. VP1 is the predominant protein present at the 5-fold axis of symmetry in the virion.

Methods of Detecting Parechovirus

The Parechovirus genus of Picornaviridae contains two known species, Human parechovirus (HPeV) and Ljungan virus (LV). The HPeVs (including the former echoviruses 22 and 23, now HPeV1 and HPeV2, respectively, as well as HPeV3) are human pathogens that cause a spectrum of disease like the enteroviruses, including aseptic meningitis, gastroenteritis, encephalitis, respiratory, and neonatal sepsis-like disease. The LVs were isolated from bank voles in Sweden, while searching for an infectious agent linked to fatal myocarditis cases in humans. Because of the decline in use of cell culture and neutralization to investigate enterovirus-like disease, very few laboratories currently have the capability to test for parechoviruses. In addition, even currently available methods for detecting parechovirus are unable to detect all known species of parechovirus in a single assay, and most require the cumbersome step of culturing the virus. Therefore, methods permitting rapid detection of all known Parechovirus species in a sample while retaining a desirable amount of specificity and sensitivity, which ideally do not require culturing of the virus, are needed.

Disclosed herein are several methods that can be used to detect all known species of Parechovirus, for example detecting parechovirus in a sample. In particular examples, the methods target amplification of a region of the 5' non-translated region (5'NTR) of the parechovirus genome. Particular examples of amplification include the real time RT-PCR Taq-Man assay and an RT-semi-nested PCR (RT-snPCR) assays. In particular examples, the method includes identifying the parechovirus species (such as HPeV or LV) or the serotype (such as HPeV1, HPeV2, HPeV3) present in the sample, for example by sequencing at least a portion of the VP1 region. However, this step can be performed independently. The availability of the disclosed methods can also be used to facilitate the identification of as yet unidentified species of parechoviruses. The methods are easily and rapidly implemented using common laboratory procedures and instrumentation. In particular examples, the methods avoid the need for cumbersome, time-consuming and resource-intensive methods, such as viral cell culture and/or host animal infection. For example, in some examples the method does not include isolating parechovirus from a cell culture prior to amplification of parechoviral cDNA. In particular examples, the disclosed methods have a sensitivity of at least 95%, a specificity of at least 95%, or both.

Provided herein are methods for detecting any Parechovirus species, such as HPeV1, HPeV2, HPeV3, and LV. In particular examples, the method includes contacting cDNA reverse transcribed from RNA isolated from a sample with a composition that permits amplification of the cDNA. Although the method can include extraction of RNA from the sample, reverse-reverse transcription of the RNA to cDNA, in some examples one or more of these steps has been previously performed. For example, if the starting material is a clinical sample, RNA is extracted and reverse transcribed, and the resulting cDNA amplified under conditions that permit amplification of at least a portion of the 5'NTR of parechovirus. If the starting material is cDNA, the cDNA is amplified using the methods disclosed herein that permit amplification of at least a portion of the 5'NTR of parechovirus.

The composition in which the amplification of cDNA occurs includes a forward primer (such as SEQ ID NO: 1) and a first reverse primer (such as SEQ ID NO: 4), wherein the forward and first reverse primers hybridize to opposite strands of a parechovirus 5'NTR. In particular examples, the regions of the 5'NTR to which the primers hybridize are conserved. The composition can further include additional agents that permit amplification of the target region of the parechovirus 5'NTR nucleic acid molecule. For example, the reaction can include dNTPs, polymerase, and $MgCl_2$.

The amplification procedure is performed under conditions that are sufficient to amplify parechovirus cDNA and produce a parechovirus amplicon from any Parechovirus species, for example if parechovirus is present in the sample. In a particular example, the parechovirus amplicon includes at least a portion of a target nucleic acid sequence, for example at least a portion of a parechovirus 5'NTR nucleic acid sequence (such as at least 15 contiguous nucleotides of a parechovirus 5'NTR, for example at least 20 contiguous nucleotides, at least 25 contiguous nucleotides, or at least 30 contiguous nucleotides of a parechovirus 5'NTR). In particular examples, the method can produce a parechovirus amplicon from at least two Parechovirus species (for example HPeV and LV), for example at least three Parechovirus species, at least four Parechovirus species, such as two, three, four, or five different Parechovirus species. In some examples, the method can produce a parechovirus amplicon from at least three Parechovirus serotypes (for example HPeV1, HPeV2, and HPeV3). Ideally, the amplification procedure produces a parechovirus amplicon that includes at least a portion of the parechovirus 5'NTR nucleic acid sequence if parechovirus is present in the sample, while not producing a detectable amplicon if parechovirus is not present in the sample. The amplification results in the production of a first reaction sample, which can contain parechovirus amplicons.

In particular examples the amplification composition also includes a probe, for example a probe of 10-50 nucleotides. The probe includes a detectable label, such as a fluorophore. The detectable label may produce a signal in the presence of a target amplicon, or result in a decreased signal in the presence of a target amplicon, depending on the particular construction of the probe. In a specific example the probe includes both a reporter fluorophore and a quencher molecule, a specific example of which is the TaqMan probe having the fluorophore on the 5'-end and the quencher on the 3'-end. In a particular example, at least a portion of the probe sequence is complementary to a region of a parechovirus 5'NTR nucleic acid sequence, for example a region located between the forward and reverse primers. Although an exemplary TaqMan probe is disclosed in SEQ ID NO: 3, one skilled in the art will appreciate that other TaqMan probes can be used (for example having a different quencher and a different fluorophore), and that other probes can be used (such as a molecular beacon) which include a sequence that is complementary to a region of a parechovirus 5'NTR.

In some examples, the method includes performing a second amplification procedure. This additional amplification can be used to further increase the number of amplicon molecules produced, for example to facilitate detection of the amplicons. For example, at least a portion of the reaction sample generated from the first amplification reaction can be incubated under conditions sufficient to amplify parechovirus cDNA and produce a parechovirus amplicon from any Parechovirus species (such as at least three different Parechovirus species or serotypes). The second amplification reaction composition can include the forward primer (such as SEQ ID NO: 1) and a second reverse primer (such as SEQ ID NO: 2). In a particular example, the second reverse primer hybridizes to the parechovirus 5'NTR upstream of where the first reverse primer hybridizes to the parechovirus 5'NTR.

Methods of amplifying a target nucleic acid sequence are known in the art. A particular exemplary amplification procedure includes polymerase chain reaction (PCR), such as real time PCR, real time quantitative PCR, or semi-nested PCR (snPCR), as well as PCR reactions which are preceded by reverse transcription (such as RT-PCR and RT snPCR).

The method also includes determining or detecting whether parechovirus amplicons were produced by the amplification reaction, for example by determining whether parechovirus amplicons are present in the first reaction sample. The presence of a detectable parechovirus amplicon indicates that at least one Parechovirus species is present in the sample (and for example that the subject from which the sample was obtained is infected with parechovirus), while the absence of a detectable parechovirus amplicon indicates that the sample does not contain parechovirus (and for example that the subject from which the sample was obtained is not infected with parechovirus).

In addition to determining whether parechovirus nucleic acid molecules are present in the sample, the method can further include quantifying the parechovirus amplicons. In one example quantitation includes comparing a signal to an amount of signal from a known amount of nucleic acid.

Methods are also provided for determining which particular Parechovirus species or serotype (or both) is present in a sample. For example, such methods can be used to determine if the subject from whom the sample was obtained is infected with HPeV1, HPeV2, HPeV3, LV, or an as yet unidentified parechovirus (or combinations thereof). Generally, the method includes determining the sequence of at least a portion of VP1 of parechovirus. Since VP1 provides sequences which are unique to particular species (and serotype) of parechovirus, determining the sequence of at least a portion of VP1 provides a means by which to determine which parechovirus is present in a sample.

In particular examples, the sample is first analyzed to determine if parechovirus is present. If the determination is made that the sample is infected with parechovirus, the method can further include determining which particular species of parechovirus is present. However, one skilled in the art will appreciate that the method can simply include determining which parechovirus species or serotype (or both) is present (for example without first determining that parechovirus is present using the methods disclosed herein). For example, if a skilled clinician makes a determination that the subject is or is suspected of having a parechovirus infection (for example based on symptoms displayed by the subject or knowledge of a parechovirus outbreak), the method can include determining which (if any) parechoviruses are present in a sample obtained from the subject.

The method for determining which particular Parechovirus species is present in a sample can include determining the sequence of at least a portion of the VP1 gene of parechovirus. In some examples, at least 200 contiguous nucleotides from a VP1 gene are sequenced, such as at least 230 contiguous nucleotides, at least 400 contiguous nucleotides, at least 600 contiguous nucleotides, or at least 800 contiguous nucleotides.

Particular examples of methods that can be used to sequence at least a portion of the VP1 gene of parechovirus are provided. However, one skilled in the art will appreciate that other methods of sequencing VP 1 can be used. In one example, cDNA is reverse transcribed from RNA isolated from a sample, for example using primers that will generate a cDNA sequence that includes the entire VP1 sequence. Exemplary primers are provided in SEQ ID NOS: 6-11. One skilled in the art will appreciate that less than the entire VP1 sequence can be generated, depending on the primers used. However, it is possible that the reverse transcription has been performed before the methods disclosed herein are used.

cDNA reverse transcribed from RNA extracted from a sample is incubated with a composition that permits amplification of the cDNA, for example permits amplification of at least a portion of parechovirus VP1 cDNA. The composition includes a forward primer (such as SEQ ID NO: 12) and a reverse primer (such as SEQ ID NO: 13), wherein the primers hybridize to opposite strands of a parechovirus nucleic acid molecule, for example to permit amplification of at least a portion of (such as all of) VP1. The amplification procedure is performed under conditions sufficient to amplify parechovirus cDNA and produce a parechovirus amplicon from any Parechovirus species, wherein the parechovirus amplicon includes at least a portion of the parechovirus VP1 nucleic acid sequence. This results in an amplification reaction sample, which ideally contains amplicons that include at least a portion of parechovirus VP1.

A second amplification reaction can be performed, for example to increase the number of amplicons. For example, at least a portion of the amplification reaction sample generated above is incubated under conditions sufficient to amplify parechovirus cDNA (such as at least a portion of VP1) and produce a parechovirus amplicon from any Parechovirus species (such as an amplicon that includes at least a portion of VP1). The amplification composition includes at least one second forward primer and at least one second reverse primer. Ideally, the primers permit amplification of at least a portion of VP1, such as at least 200 contiguous nucleotides of VP1.

In a particular example, the primers are used in pairs (2 primers per reaction), with alternative pairs being used depending upon the portion of VP1 to be amplified and sequenced. For example, the primers shown in SEQ ID NOS: 12 and 13 amplify the complete VP1 plus part of VP3 and part of 2A. This results in an amplicon of about 990 nucleotides. Because it can be difficult to directly sequence an amplicon of this length, an alternative method is to amplify two overlapping fragments (for example using the primers shown in SEQ ID NOS: 12 and 14 in one reaction and primers shown in SEQ ID NOS: 15 and 16 in another reaction), sequencing each amplicon individually and assembling the complete sequence from the two overlapping sequences. Alternatively, for identification purposes, it can be sufficient to sequence only a portion of VP1, such as the amplicon generated using primers SEQ ID NOS: 15 and 14.

The amplicons resulting from the second amplification reaction are sequenced, using methods known in the art. Based on the VP1 nucleotide (or corresponding protein) sequence (or at least a portion thereof, such as at least 230 contiguous nucleotides or at least 75 amino acids), a determination is made as to which parechovirus species the VP1 sequence encodes. For example, the method can include comparing the obtained sequence to a database containing parechovirus VP1 sequences (such as EMBL or GenBank). Based on the percent sequence identity between the obtained VP1 sequence and the VP1 sequence in the database, the species of parechovirus present can be determined. In particular examples, if the two nucleotide sequences have greater than 75% sequence identity or have greater than 85% amino acid sequence identity, they are the same type. For example, if the nucleotide sequence of the amplicon has 85% sequence identity to LV, then it is concluded that the sample (and the subject from whom the sample was obtained) is infected with LV. In particular examples, if two nucleotide sequences are less than 70% identical, this indicates that the species is a "new" or previously unidentified (or unsequenced) Parechovirus species. For example, if the nucleotide sequence of the amplicon has 50% sequence identity to HPeV or LV, then it is concluded that the sample (and the subject from whom the sample was obtained) is infected with a new strain of parechovirus. In particular examples, if two nucleotide sequences are 70-75% identical, the result is inconclusive as to the species or serotype, but having greater than 45% sequence identity (such as 46-75% sequence identity) indicates that the sample is infected with a parechovirus.

Clinical Samples

Samples containing nucleic acid molecules (such as viral RNA) can be obtained from any appropriate biological specimen, for instance stool samples, fluids (such as CSF), tissue samples (such as a lung or spleen tissue sample), or swabs (such as a nasopharyngeal swab). Techniques for acquisition of such samples are well known in the art.

Exemplary samples include, but are not limited to: whole blood or a fraction thereof, a bronchial wash, CSF, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, or tissue from an experimentally infected animal. In a particular example, the sample is a stool specimen, CSF, or a nasopharyngeal swab. In some examples, two or more samples from a subject are analyzed for the presence of *parechovirus*.

Once a sample has been obtained, the sample can be used directly, concentrated (for example by centrifugation or filtration), purified, or combinations thereof. In particular examples, RNA is extracted directly from the sample.

Isolation of RNA

In some examples, the method includes isolating RNA from the sample. However, the RNA may have been previously isolated. RNA can be isolated from a sample using methods known in the art, thereby yielding an RNA preparation that is accessible to, and amenable to, generation of cDNA (for example by reverse transcription PCR). Isolating relates to releasing RNA from a latent or inaccessible form in a virion or a cell and allowing the RNA to become freely available. In such a state, for example, it is suitable for effective amplification by reverse transcription and use of the polymerase chain reaction.

Isolating RNA can include steps that achieve the disruption of virions (such as parechovirus) containing viral RNA, as well as disruption of cells that may harbor such virions (such as cells present in a sample). Isolation of RNA is generally performed under conditions that effectively exclude or inhibit ribonuclease activity that may be present. Additionally, isolation of RNA cam include steps that achieve at least a partial separation of the RNA dissolved in an aqueous medium from other cellular or viral components, wherein such components can be either particulate or dissolved. In a particular example, RNA is isolated using a commercially available kit (such as the QIAamp Viral RNA Mini Kit, Qiagen, Inc., Valencia, Calif.).

Reverse Transcription

The RNA isolated from a clinical sample can be converted to cDNA using reverse transcriptase. Reverse transcription (RT) relates to a procedure catalyzed by an enzyme activity, reverse transcriptase, which synthesizes a cDNA from a single stranded RNA molecule, with the use of oligonucleotide primers having free 3'-hydroxyl groups. Commercially available kits can be used.

In particular examples, reverse transcription is performed in the same composition that amplification is performed in (such as RT-snPCR).

Primers

Primers are oligonucleotides that have a nucleotide sequence which is complementary to at least a portion of a target nucleic acid molecule, such as at least a portion of parechovirus 5'NTR or parechovirus VP1 nucleic acid sequence. When the primer is caused to hybridize to the specific sequence in a nucleic acid molecule to which it is complementary, it may serve as the priming position, or the initiation position, for the action of a primer-dependent polymerase activity. The primer, once hybridized, acts to define the 5' end of the operation of the transcription activity of the polymerase on the duplex. Commonly in PCR, a specific pair of primers is employed, wherein one of the primers hybridizes to one end and the second primer hybridizes to the other end. The primers hybridize in such an orientation that transcription, which proceeds in the direction from 5'- to 3'-, is in the direction leading from each primer toward the site of hybridization of the other primer. After several rounds of hybridization and transcription the amplified nucleic acid molecule produced is a segment having a defined length whose ends are defined by the sites to which the primers hybridize.

The oligonucleotide primers disclosed herein can be used in reverse transcription or PCR amplification of a target segment of a nucleic acid from a parechovirus (such as 5'NTR or VP1). Both RT and PCR rely on the action of a DNA polymerase activity to extend the new DNA strands beyond the 3' termini of the primers. Since DNA polymerases extend a chain in the direction from 5' to 3', an oligonucleotide that contains sequences in addition to those nucleotides that hybridize to the target nucleic acid and serve as the primer have the primer sequence at the 3' end of the oligonucleotide. Additionally, complements of the primers disclosed herein have the sequence complementary to the hybridizing sequence at the 5' end of the molecule such that action of a DNA polymerase will generate a primer oligonucleotide having its complementary sequence at its 3' end.

Probes

Probes can be included in an amplification reaction, for example to permit detection of formed amplicons (such as in real time). In one example, the detectable label associated with the probe is a fluorophore. The fluorescence signal intensity can be related to the amount of PCR product (amplicon) by a product-dependent decrease of the quench of a reporter fluorophore, or by an increase of the Förster resonance energy transfer (FRET) from a donor to an acceptor fluorophore. FRET is the radiationless transfer of excitation energy by dipole-dipole interaction between fluorophores with overlapping emission and excitation spectra. Because the FRET and the quench efficiency are strongly dependent on the distance between the fluorophores, the PCR-product-dependent change in the distance between the fluorophore can be used to generate the sequence-specific signals.

Several different probes can be used to practice the disclosed method. For example, as an alternative to using TaqMan probes, other types of probes known in the art and disclosed herein can be generated which are complementary to a similar or the same region of 5'NTR of SEQ ID NO: 3. In addition, all could function by a decrease of quench or an increase of FRET. Exemplary quenchers include, but are not limited to TAMRA (6-carboxy-tetramethylrhodamine), DABCYL (4-(4-dimethylaminophenylazo)benzoic acid)? and the Black Hole Quencher® (BHQ, Biosearch Technologies, Novato, Calif.). BHQ, a non-fluorescent quencher (NFQ) can quench most commonly used fluorophores, and does not fluoresce itself.

In one example, 5' nuclease fluorogenic target-specific oligonucleotide probes are utilized. One particular example of such a probe is a TaqMan probe (Applied Biosystems, Foster City, Calif.), which includes a reporter fluorophore at the 5' end, and quencher internally or at the 3' end. An exemplary 5' reporter fluorophore is FAM and an exemplary 3' quencher fluorophore is TAMARA. Intact probes do not produce a fluorescent signal, because they are quenched. In one example, during extension of the primers, the TaqMan probe, which is complementary to the amplicon sequence, is bound to the single-stranded PCR product like the primers. Upon reaching the probe, Taq DNA polymerase cuts the probe, releasing the quencher from the reporter fluorophore, which now fluoresces after excitation with the appropriate wavelength of light. The signal generated by the reporter fluorophore is detected, and quantitation of the amplicons can be made by analysis of the resulting amplification curve.

In particular examples, a target-specific oligonucleotide TaqMan probe (such as one that is complementary to a region of a parechovirus 5'NTR) is about 20-40 nucleotides, has a GC content of about 40-60%, has no repeated sequence motifs, and in some examples has no runs of a single nucleotide.

Another example of fluorogenic target-specific oligonucleotide probes is molecular beacons. Molecular beacons include a reporter fluorophore on one end, and a quencher (such as DABCYL) on the other end. Only the middle of the probe is complimentary to the amplicon sequence (such as a region that recognizes at least a portion of parechovirus 5'NTR), and the terminal 10-15 nucleotides are self-complementary. In its free state, the probe forms a hairpin structure whereby the reporter is close to the quencher. However, during the annealing phase of the PCR, the loop can hybridize to the PCR product, thereby opening the stem and relieving the quenching. The fluorescence emitted by the reporter molecule is detected during each annealing cycle, and quantitation of the amplicons can be made by analysis of the resulting amplification curve.

Light-up probes can also be used as fluorogenic target-specific oligonucleotide probes. Light-up probes are peptide nucleic acid molecules that use thiazole orange as the fluorophore. A quencher is not required. Upon hybridization of the light-up probe with the target nucleic acid molecule, duplex or triplex molecules are formed with increased fluorescence intensity of the fluorophore.

Another example of fluorogenic target-specific oligonucleotide probes is sunrise primers (commercially available as Ampliflour hairpin primers). Sunrise primers include a 5'-terminal hairpin, labeled with a reporter fluorophore and a quencher. The hairpin keeps the reporter and quencher together. As the forward primer, the sunrise primer is extended. This extended product serves as a template for the reverse primer in the next step. Eventually, the polymerase opens the hairpin, and a ds PCR product is formed, in which the reporter and quencher are separated. The fluorescence emitted by the reporter is detected, and quantitation of the amplicons can be made by analysis of the resulting amplification curve.

Yet another example of fluorogenic target-specific oligonucleotide probes is scorpion primers. Although similar to molecular beacons described above, they serve as primers in the PCR reaction. Scorpion primers include self-complementary sequences that form a 5'-terminal stem-loop structure, which the loop sequence is complementary to the amplicon sequence. The 3' end serves as the primer. The stem region is labeled with a reporter fluorophore and a quencher. The primer is extended, thereby forming a template for the reverse primer. The stem then opens and the loop binds to the product, separating the reporter and quencher. In contrast to sunrise primers, the reverse extension is blocked by a hexethylene glycol group, to ensure that the reporter of the scorpion primer remains quenched in unspecific products like primer dimers. The fluorescence emitted by the reporter is detected, and quantitation of the amplicons can be made by analysis of the resulting amplification curve.

Therefore, the primers shown in SEQ ID NOS: 1, 2, 4, 12, 13, 14, 15, or 16 can be redesigned as sunrise or scorpion primers, using methods known in the art.

Amplification of Nucleic Acids

Any amplification method known in the art can be used to amplify at least a portion of the 5'NTR or VP1. Particular examples include, but are not limited to: real-time PCR (for example see Mackay, *Clin. Microbiol. Infect.* 10(3):190-212, 2004), nested PCR, semi-nested PCR, real time quantitative PCR, Strand Displacement Amplification (SDA) (for example see Jolley and Nasir, *Comb. Chem. High Throughput Screen.* 6(3):235-44, 2003), self-sustained sequence replication reaction (3SR) (for example see Mueller et al., *Histochem. Cell. Biol.* 108(4-5):431-7, 1997), ligase chain reaction (LCR) (for example see Laffler et al., *Ann. Biol. Clin. (Paris)*.51(9):821-6, 1993), transcription mediated amplification (TMA) (for example see Prince et al., *J. Viral Hepat.* 11(3):236-42, 2004), or nucleic acid sequence based amplification (NASBA) (for example see Romano et al., *Clin. Lab. Med.* 16(1):89-103, 1996).

Real-time PCR is a particular example of an in vitro amplification method, for example enabled by Applied Biosystems (TaqMan PCR). Real-time quantitative TaqMan PCR allows the routine and reliable detection (and in some examples quantification) of PCR products (such as parechovirus amplicons) to produce sensitive, accurate, and reproducible measurements of levels of nucleic acids molecules present. During amplification, annealing of the probe to its target sequence (such as the parechovirus 5'NTR) generates a substrate that is cleaved by the 5' nuclease activity of Taq DNA polymerase when the enzyme extends from an upstream primer into the region of the probe. This dependence on polymerization ensures that cleavage of the probe occurs only if the target sequence is being amplified.

RT-semi-nested PCR uses reverse transcription and amplification steps as in conventional PCR, but a second amplification reaction is performed using a portion of the first reaction as template, to increase the yield of amplicons. For the second amplification of semi-nested PCR (also known as hemi-nested PCR), one of the primers is the same as one of those used in the first amplification reaction and the other primer is complementary to a sequence internal to the first reaction amplicon, such that the two primers extend toward one another and produce a product that is shorter than the first reaction amplicons (because the primers are closer together). In nested PCR, both primers are internal to the first reaction product and chosen such that the two primers extend toward one another and produce a product that is shorter than the first reaction amplicons (because the primers are closer together).

Detection

Methods of detecting an amplicon are known in the art. In a particular example, detection includes detecting a change in detectable signal from a label, such as detecting fluorescence (such as fluorescence from a fluorophore associated with a probe), such as an increase or decrease in fluorescence. The detectable signal changes in a predictable manner that permits determination of whether or not a target nucleic acid sequence (such as a parechovirus amplicon) is present in a sample, and in some examples, quantitation of an amount of target nucleic acid sequence present in a sample. In particular examples, the presence of detectable fluorescence (such as an increase in fluorescence) indicates that parechovirus amplicons are present and that the sample contains parechovirus, and the absence of detectable fluorescence (such as no significant increase in fluorescence) indicates that parechovirus amplicons are not present and that the sample does not contain parechovirus. In particular examples, the change in signal is compared to a signal present earlier, such as prior to nucleic acid amplification.

Detection of amplicons can be achieved by monitoring a change in signal during the amplification reaction, for example in real time as the amplicons are formed (for example when real time PCR is used). For example, the label present on the probe present in the amplification reaction will generate a significant signal or not when the probe is freely floating in the nucleic acid amplification reaction mixture. During nucleic acid amplification, the signal from the label associated with the probe will increase or decrease. As more amplicons are produced during nucleic acid amplification, the overall signal of the reaction mixture will increase or decrease. The change in signal can be monitored using any commercially available system, and permits detection of a target nucleic acid sequence in the reaction.

In one example, for example when the probe is a TaqMan probe, the change in signal monitored during the amplification reaction is an increase in fluorescence. The fluorescence of the dye is quenched when the probes are freely floating in the nucleic acid amplification reaction mixture. During nucleic acid amplification, the fluorescence increases due to the degradation of the probe and resulting release of the reporter fluorophore (and separation of the quencher from the fluorophore). As more amplicons are produced during nucleic acid amplification, the overall fluorescence of the reaction mixture increases. The increase in fluorescence can be measured and observed, for example by using a commercially available nucleic acid amplification system capable of measuring fluorescence (such as real-time PCR thermocyclers). An increase in fluorescent signal indicates the presence of a target nucleic acid sequence in the reaction, such as *parechovirus* amplicons. In other examples, the change in signal that is monitored during the amplification reaction is a decrease in fluorescence.

One skilled in the art will recognize that instead of using a nucleic acid molecule that includes a detectable label as the probe, SYBR-green or similar intercalating dyes can be used to detect the resulting amplicon molecules.

In other examples, detection of amplicons occurs following the amplification reaction (for example when RT-snPCR is used). For example, the resulting amplification reaction can be analyzed using include gel electrophoresis and visualization of amplicons contained in a resulting gel, size separation matrix, capillary electrophoresis and detection of the emerging amplicon, probing for the presence of the parechovirus amplicon using a probe, or sequencing the parechovirus amplicon.

Nucleic Acid Molecules

The present disclosure provides nucleic acid molecules, such as probes and primers, which can be used to practice the methods disclosed herein.

Provided herein are isolated nucleic acid molecules, such as those comprising or consisting of the nucleic acid sequence provided in any of SEQ ID NOS: 1, 2, 3, 4 or 6-16. Although particular probe and primer sequences are provided, one skilled in the art will appreciate that small changes, such as substitution, deletion, or addition of 1-2 nucleotides to any of SEQ ID NOS: 14 or 6-16, can be made to the disclosed sequences. For example, an isolated nucleic acid molecule can have at least 95% sequence identity to SEQ ID NO: 2, wherein the nucleic acid molecule retains the ability to hybridize to a parechovirus 5'NTR sequence under very high stringency conditions. However, one skilled in the art will appreciate that larger numbers of changes (such as 3-10 insertions, deletions, substitutions or combinations thereof) can be made to the disclosed primers for example if using a sunrise or scorpion primers based on SEQ ID NOS: 1, 2, 4, or 6-16.

In addition, although a particular exemplary TaqMan probe is provided in SEQ ID NO: 3, one skilled in the art will appreciate that other probes that are complementary to the same region of parechovirus 5'NTR can be generated using methods known in the art. For example, molecular beacons or light-up probes can be generated that recognize the same region of parechovirus 5'NTR as SEQ ID NO: 3, and used in the disclosed methods to detect amplicons. Such different probes may require changes of more than 1-2 nucleotides, for example addition of 1-20 nucleotides. In addition, the TaqMan probe shown in FIG. 3 can be modified to change the particular quencher and fluorophore used (for example changing BHQ and Yakima Yellow to TAMRA and FAM, respectively).

Kits

The present disclosure provides kits that include one or more of the nucleic acid molecules provided herein. For example, the kit can include probes or primers that permit detection of parechovirus in a sample, such as one or more of SEQ ID NOS: 1-4. For example, the kit can include forward and reverse primers, such as SEQ ID NO: 1 and 4, and in some examples a probe, such as SEQ ID NO: 3.

In some examples, the kits also include primers used to determine which particular species of Parechovirus is present in the sample. For example, the kit can include forward and reverse primers that can be used to amplify at least a portion of a parechovirus VP1 nucleic acid sequence of (for example one or more of SEQ ID NOS: 6-16).

In a particular example, the kit includes 2, 3, 4, 5, 6, 7, 8, 9, 10, 11, 12, 13, 14 or 15 of the disclosed nucleic acid molecules, such as a kit that includes SEQ ID NO: 1, for example a kit that includes SEQ ID NOS: 1 and 4, a kit that includes SEQ ID NO: 1, 3 and 4, or a kit that includes SEQ ID NOS: 1, 2 and 4. Exemplary combinations of probes and primers that can be included in a kit are shown in Table 1. However, one skilled in the art will appreciate that the probes in the kit can include other fluorophores and quenchers in addition to the particular combinations disclosed herein.

TABLE 1

Exemplary kits.

| Kit Number | SEQ ID NOS: Present |
|---|---|
| 1 | 1, 4 |
| 2 | 1, 3, 4 |
| 3 | 1, 2, 4 |
| 4 | 6-11 |
| 5 | 12, 13 |
| 6 | 12, 14 |
| 7 | 15, 16 |
| 8 | 14, 15 |
| 9 | 6-15 |
| 10 | 12, 13, 14, 15 |
| 11 | 1, 3, 4, 6-15 |
| 12 | 1, 3, 4, 12, 13, 14, 15 |

In addition to nucleic acid molecules, the kits can further include one or more agents for reverse transcription, one or more agents for amplification of cDNA, or combinations thereof. For example, the kit can further include Taq polymerase, dNTPs, buffers, reverse transcriptase, and the like.

Example 1

Primers for Detection of *Parechovirus*

This example describes primers that can be used to detect all known species of the Parechovirus genus, including HPeV1, HPeV2, HPeV3, and LV. Although particular examples of primers are provided, one skilled in the art will recognize that small modifications (such as variations in 1-2 nucleotides, for example 1-2 substitutions, deletions or additions) can be made to these sequences, without losing the ability to detect parechoviruses.

Figure 1:
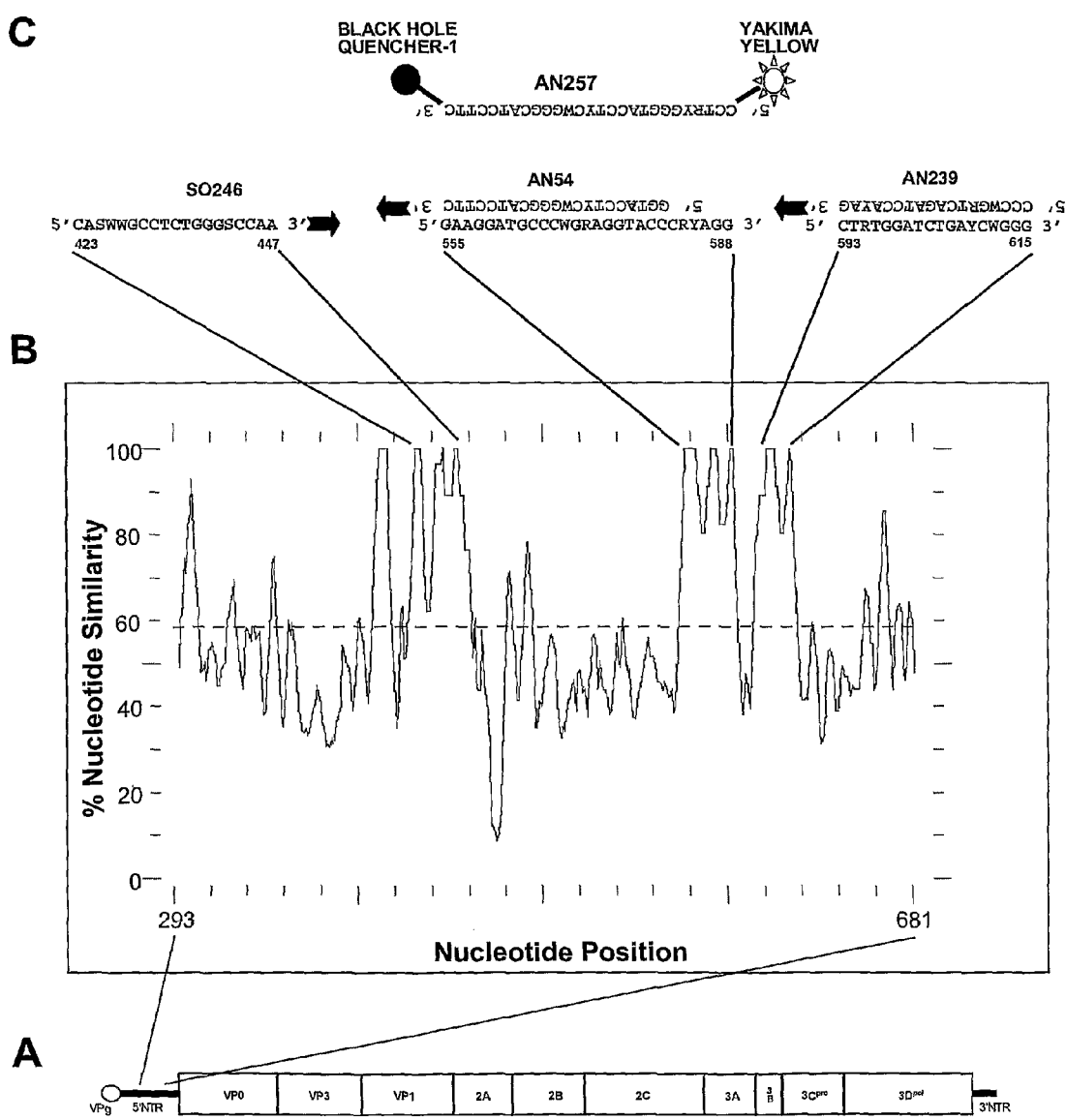
FIG. 1A is a schematic representation of the parechovirus genome, showing the location of the 5' non-translated region (NTR) used to design probes and primers for detecting parechoviruses.
FIG. 1B is a similarity plot showing a region of the 5'NTR of five human parechoviruses and five Ljungan viruses. Sequences were aligned with Pileup (Wisconsin Sequence Analysis Package, Genetics Computer Group, Madison, Wis.), and the average similarity across the entire alignment was determined, using PlotSimilarity (Wisconsin Sequence Analysis Package) with a window of five nucleotides. Similarity scores of 100% indicate nucleotide sequence identity among all 10 parechoviruses.
FIG. 1C is a schematic diagram showing the sequence and location of the primer (SEQ ID NOS: 1, 2, and 4) and probe (SEQ ID NO: 3) sites. The numbering of the primer nucleotide positions is relative to the published sequence of HPEV1-Harris and are for orientation only. IUB ambiguity codes: R=A or G, Y=C or T, W=A or T, S=C or G.

Primers and a probe having homology to the 5'NTR of the parechovirus genome were designed as shown in FIGS. 1A-C:

```
5'-CASWWGCCTCTGGGSCCAA-3' (forward primer, SEQ ID
NO: 1);

5'-GGTACCTYCWGGGCATCCTTC-3' (semi-nested reverse
primer, SEQ ID NO: 2);

5'-CCTRYGGGTACCTYCWGGGCATCCTTC-3' (probe having a
5' fluorophore and a 3' quencher, SEQ ID NO: 3);
and 5'-CCCWGRTCAGATCCAYAG-3' (reverse primer, SEQ ID
NO: 4).
```

Variants of SEQ ID NOS: 1-4 can be generated and used in the methods described herein. For example, if the 3' 5-8 nucleotides are intact, the primers can tolerate 1-5 mismatches in their 5' portion.

Example 2

RNA Extraction

This example describes methods used to extract RNA from biological samples. Although particular methods are described, one skilled in the art will recognize that other methods of extraction known in the art can be used. In addition, similar methods can be used on any biological sample.

Virus isolates and nasopharyngeal swabs were extracted with the QIAamp Viral RNA Mini Kit (Qiagen, Inc., Valencia, Calif.), which was used according to the manufacturer's instructions. Stool suspensions and rectal swabs were extracted with an equal volume of Vertrel XF (Miller-Stephenson Chemical Co., Danbury, Conn.) prior to using the QIAamp kit. Tissues were homogenized in 500 µl Tri-Reagent (Sigma, St. Louis, Mo.) and then extracted with 200 µl chloroform. The emulsion was centrifuged and the aqueous phase transferred to a fresh tube. The RNA was precipitated with 3 volumes of isopropanol and 2 µl Pellet Paint Co-Precipitant (Novagen, Madison, Wis.), pelleted and washed. The RNA was resuspended in 30-60 µl nuclease-free water.

For CSF samples, 140 µl CSF was digested with 20 µg proteinase K for 30 minutes at 37° C. prior to using the QIAamp kit and eluting the RNA in 60 µl nuclease-free water.

Example 3

Amplification of Parechoviral Nucleic Acid Molecules

This example describes amplification methods that can be used to detect all known Parechovirus species, such as HPeV1, HPeV2, HPeV3, and LV. Although particular conditions are provided, one skilled in the art will appreciate that variations can be made (such as increasing or decreasing the number of PCR cycles), while still permitting amplification and detection of parechoviral nucleic acid molecules. Both the real time PCR and semi-nested PCR methods target conserved regions in the 5'NTR of the parechovirus genome and share forward and reverse primers. The Taqman probe and RT-snPCR nested primer target the same conserved site but vary in length. It is shown herein that the RT-snPCR method is slightly more sensitive than the Taqman assay, but both are more sensitive than cell culture and either method can be used to analyze isolates or original clinical samples.

All real-time PCR assays were run on a Stratagene Mx4000 Multiplex Quantitative PCR System with version 4.20 analysis software. Standards were run in triplicate and averaged before standard curve plotting, using the least mean squares curve fitting algorithm.

One-Step Real Time PCR

The following methods were used to amplify parechoviral nucleic acid molecules using one-step (OS) real-time PCR. Using this method, RNA extracted from the sample (Example 2) is reverse transcribed to cDNA and the cDNA amplified in a single reaction. The QuantiTect Probe RT-PCR kit (Qiagen, Inc.) was used according to the manufacturer's instructions with primers shown in SEQ ID NOS: 1 and 4 and 0.2 µM of the Taqman probe shown in SEQ ID NO: 3, in a total reaction volume of 50 µl. For virus isolates, 1 µl of RNA was used. For sensitivity assays and for clinical specimens, 5 µl of RNA was used. cDNA was generated from the extracted RNA by incubation at 50° C. for 30 minutes then 95° C. for 15 minutes. The resulting cDNA was amplified using PCR amplification conditions of 50 cycles of 95° C. for 20 seconds, 55° C. for 40 seconds, and 72° C. for 20 seconds.

Because a Taqman probe was used (SEQ ID NO: 3), amplified cDNA was detected in real time by detecting fluorescence from the fluorophore on the 5'-end of the probe. In this example, Yakima Yellow™ was used, which has absorption and emission maximum wavelengths respectively of 525 nm and 548 nm. If parechoviral RNA was present in the sample, an increase in fluorescence was observed, due to cutting of the probe, thereby releasing the quencher on the 3'-end of the probe from the 5'-reporter fluorophore. In the absence of parechoviral RNA in the sample, no or minimal fluorescence (such as background levels) was observed, since the probe remains intact, allowing the quencher to quench the fluorescent signal of the 5'-reporter fluorophore.

Two-Step Real Time PCR

The following methods were used for two-step (TS) real-time PCR. In this method, synthesis of the cDNA from the extracted RNA (Example 1) is separate from the amplification reaction. Synthesis of cDNA was performed in a 10 µl reaction containing 5 µl of extracted RNA, 100 mM each dNTP, 2 µl of 5× reaction buffer (Invitrogen, Carlsbad, Calif.), 0.01 M dithiothreitol, 1 pmol of SEQ ID NO: 4, 20 U of RNasin (Promega, Madison, Wis.), and 100 U of Superscript II reverse transcriptase (Invitrogen). cDNA was reverse transcribed from RNA by incubation at 42° C. for 10 minutes; 50° C. for 40 minutes; and 95° C. for 5 minutes.

For the real-time PCR, the Quantitect Probe PCR Kit (Qiagen) was used according to the manufacturer's protocol, with 0.4 µM of each primer shown in SEQ ID NO: 1 and 4. The entire 10 µl cDNA reaction was used in the PCR. The probe concentration of SEQ ID NO: 3 was 0.2 µM in a total reaction volume of 50 µl. The resulting cDNA was PCR amplified as follows: 95° C. for 15 minutes (to inactivate the RT), then 50 cycles of 95° C. for 20 seconds; 55° C. for 40 seconds, and 72° C. for 20 seconds. During the PCR amplification, fluorescence was detected in real time as described above.

Reverse Transcription-Semi-Nested PCR

The following methods were used for reverse transcription-semi-nested PCR (RT-snPCR). This method was used to increase the number of copies of parechoviral nucleic acid molecules, and can be used to increase the analytical sensitivity of the method. Synthesis of cDNA from the extracted RNA (Example 2) was performed as described above for the TS real-time assay.

The entire cDNA reaction was used in the first PCR reaction (total of 50 l), which included of 5 µl of 10×PCR buffer (Roche Applied Science, Indianapolis, Ind.), 200 μM each dNTP, 20 μmol of primers SEQ ID NO: 1 and SEQ ID NO: 4, and 2.5 U Taq DNA polymerase (Roche). The amplification conditions were as follows: 95° C. for 15 minutes, then 50 cycles of 95° C. for 30 seconds; 55° C. for 30 seconds; and 72° C. for 30 seconds.

The second semi-nested PCR (total of 50 μl) consisted of 1 μl of the first PCR reaction in a reaction containing 5 μl of 10× FastStart Taq Buffer (Roche), 200 μM each dNTP, 20 μmol of primers shown in SEQ ID NO: 1 and 2, and 2.5 U of FastStart Taq polymerase (Roche). The amplification conditions were as follows: 95° C. for 15 minutes, then 50 cycles of 95° C. for 30 seconds; 55° C. for 30 seconds; and 72° C. for 30 seconds.

The resulting amplicons were detected by separation on a 1.5% agarose gel followed by staining with 0.5 μg/ml ethidium bromide and visualization by UV transillumination.

Standards

Synthetic RNA standards were made using the MEGAscript High Yield Transcription Kit (Ambion, Austin, Tex.) according to the manufacturer's protocol. The resulting single-stranded, positive-sense standard RNA products (HPeV1 Harris, 860 bases, and LV SWE 87-012, 890 bases) were purified and quantitated; the concentration calculated in units of RNA molecules per microliter.

Results

Figure 2:
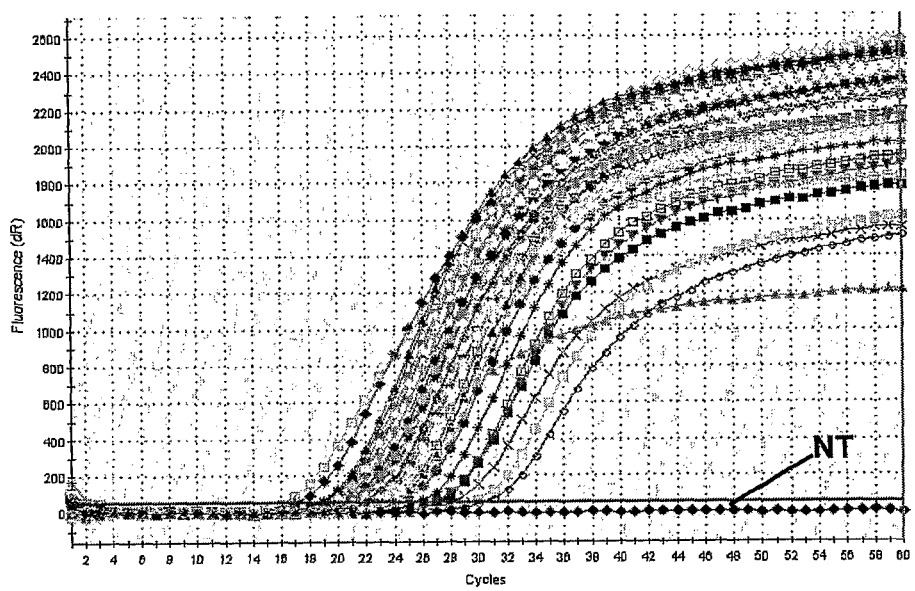
FIG. 2 is an amplification plot of 47 HPeV isolates (including HPeV1, HPeV2, and HPeV3) using the parechovirus 5'NTR one step real-time PCR method. NT=no template control.

Specificity was determined by amplifying 47 HPeV clinical isolates from the CDC picornavirus collection, including prototypes HPeV1-Harris and HPeV2-Williamson and two field isolates of HPEV3. The prototype LV-SWE87-012 and three other LV strains, including SWE174F, SWE145SL, and OR62-M1146, were also used. As shown in Table 2, all three of the parechovirus 5' NTR PCR based methods were able to amplify all of the HPeV and LV isolates. Therefore, the specificity using any one of the three methods was 100%. The amplification plot for the HPeV one-step (OS) real-time PCR is shown in FIG. 2.

TABLE 2

Specificity of amplification methods.

| Virus | OS Real Time PCR* | TS Real Time PCR* | RT-snPCR |
|---|---|---|---|
| HPeV | 47/47 | 46/47 | 47/47 |
| LV | 4/4 | 4/4 | 4/4 |

*OS = One-Step and TS = Two-Step.

In a study of 243 CSFs submitted to virology laboratory of The Children's Hospital (TCH) (Denver, Colo.) during 2005, 14 EV and 13 HPeV (all HPeV3) were detected (see Example 6, below). Nine of the 14 EV detections were also detected at the time of clinical treatment, using a PCR assay d. All EV and HPeV detections were specific, as confirmed by sequencing.

Sensitivity was determined using two methods. Sensitivity relative to cell culture infectivity was measured using titered stocks of prototype strains HPeV1 Harris and LV SWE87-012. RNA was extracted from the stocks using the QIAamp Viral RNA kit and 140 μl cell culture supernatant serially diluted to contain from $10^4$ CCID50 to $10^{-3}$ CCID50 per 5 μl. PCR reactions were run in triplicate for all three PCR methods. The results are shown in Table 3. The sensitivity relative to cell culture infectivity for all three parechovirus 5'NTR methods is shown in units of cell culture infectious dose 50% endpoint units (CCID50) for two parechovirus prototype strains. The parechovirus 5'NTR OS and TS real-time methods were all linear over the detectable range. All three PCR methods were more sensitive than cell culture, by a factor of 10-100 (1 CCID50 is the amount of virus needed to infect 50% of inoculated cell cultures; for example, in ten replicates, 5 would be positive and 5 negative, the PCR methods detect $\frac{1}{10}$ to $\frac{1}{100}$ that amount of virus).

TABLE 3

Sensitivity relative to cell culture infectivity of amplification methods.*

| Virus | OS Real Time PCR | TS Real Time PCR | RT-snPCR |
|---|---|---|---|
| HPeV 1 Harris | 0.1 $CCID_{50}$ ($r^2 = 0.997$) | 0.01 $CCID_{50}$ ($r^2 = 0.994$) | 0.1 $CCID_{50}$ |
| LV SWE 87-012 | 0.1 $CCID_{50}$ ($r^2 = 0.999$) | 0.01 $CCID_{50}$ ($r^2 = 0.985$) | 0.01 $CCID_{50}$ |

*The $r^2$ values are shown in parentheses for each real-time standard curve.

Figure 3:
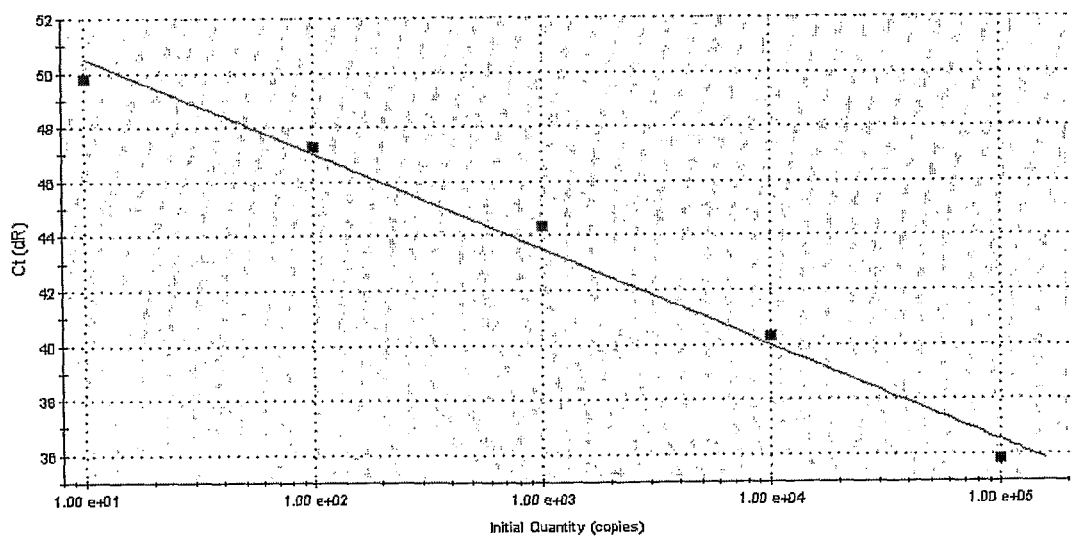
FIG. 3 is a standard curve of the LV SWE87-012 absolute sensitivity using the two-Step (TS) Real-Time PCR. PCR reactions were run in triplicate for each dilution of sRNA. The $r^2$ value for this curve=0.985.

Absolute sensitivity was measured by using in vitro-transcribed synthetic RNA standards (sRNA) derived from prototype strains HPeV1-Harris and LV-SWE87-012. sRNA standards were diluted to contain from $10^5$ to 1 copy per 5 μl. PCR reactions were run in triplicate for all three PCR methods. The results are shown in Table 4. An example standard curve for the LV-SWE87-012 two-step (TS) real-time PCR is shown in FIG. 3. The three methods varied in absolute sensitivity, the RT-snPCR detecting as little as 1 molecule of LV RNA (10 molecules of HPeV1 RNA), while the OS real-time assay detected as little as 1000 molecules of either HPeV or LV RNA.

TABLE 4

Absolute sensitivity of amplification methods.*

| sRNA | OS Real Time PCR | TS Real Time PCR | RT-snPCR |
|---|---|---|---|
| HPeV 1 Harris | $10^3$ copies ($r^2 = 0.997$) | $10^3$ copies (r2 = 1.00) | 10 copies |
| LV SWE 87-012 | $10^3$ copies ($r^2 = 0.983$) | 10 copies ($r^2 = 0.985$) | 1 copy |

*The $r^2$ values are shown in parentheses for each real-time standard curve.

Example 4

Analysis of Clinical Specimens

This example describes methods used to determine if clinical samples were infected with parechovirus. Although the RT-snPCR method described in Example 3 was used, it is appreciated that the other amplification methods described herein can be used. In addition, similar methods can be used to analyze other types of samples for the presence of parechovirus.

The RT-snPCR method was used to analyze 83 human and 6 porcine stool specimens from a possible zoonotic outbreak in South America. The specimens were collected during a seasonal, recurring, non-polio acute flaccid paralysis (AFP) outbreak in humans temporally associated with similar disease in domestic pigs. RNA was extracted from the samples using the methods in Example 2, and cDNA generated and amplified using the RT-snPCR method described in Example 3.

27 specimens (23 humans and 4 pigs) were found to be parechovirus-positive using these methods. The 5'NTR PCR amplicons from the positive specimens were sequenced to confirm that the amplicons were parechovirus and not false-positive PCR products. The 25 (of 27-two sequence failures; two of the sequencing reactions may have failed due to insufficient template) parechovirus sequence-confirmed stool specimens were then assayed with the parechovirus OS and TS Real Time PCR methods (Example 3) to determine efficacy from stool and the relative sensitivity between the methods (Table 5, 21 human and 4 porcine stool specimens). As shown in Table 5, RT-snPCR was more sensitive than both of the real-time PCR methods (about 68% sensitive relative to RT-snPCR).

TABLE 5

Sensitivity of detection of parechoviruses in stool specimens.

| OS Real Time PCR | TS Real Time PCR | RT-snPCR |
|---|---|---|
| 17/25 | 17/25 | 25/25 |

Autopsy samples previously obtained from three infants were analyzed as follows. Viruses with enterovirus-like cytopathic effect (CPE) in Vero cells were isolated from rectal swabs in two cases and from rectal swab and lung tissue in one case. All three viruses tested enterovirus-negative, and were identified as HPeVs using parechovirus VP1 sequencing (see Example 6). In one case the virus was determined to be a serotypically uncharacterized virus, and the viruses from the other two cases were identified as HPeV3. Subsequently, original autopsy rectal (RS) and nasopharyngeal (NP) swabs, and lung and spleen tissues were analyzed for the presence of parechovirus using the RT-snPCR methods described in Example 3. The results are shown in Table 6.

TABLE 6

Analysis of samples by all three parechovirus methods.*

| | OS Real Time PCR | TS Real Time PCR | RT-snPCR | Virus Isolation |
|---|---|---|---|---|
| Case 1 7 wk/M | | | | |
| Lung | Negative | Negative | Positive | Positive |
| RS | Positive $10^{5.1}$ copies | Positive $10^{5.4}$ copies | Positive | Positive |
| Case 2 16 mo/F | | | | |
| Lung | Negative | Negative | Positive | Negative |
| Spleen | Positive $10^{3.9}$ copies | Negative | Positive | Negative |
| NP | Positive $10^{3.7}$ copies | Positive $10^{3.9}$ copies | Positive | Negative |
| RS | Negative | Negative | Positive | Positive |
| Case 3 2 mo/M | | | | |
| Lung | Negative | Negative | Negative | Negative |
| Spleen | Negative | Negative | Positive | Negative |
| NP | Positive $10^{4.5}$ copies | Negative | Positive | Negative |
| RS | Positive $10^{4.9}$ copies | Positive $10^{5.2}$ copies | Positive | Positive |

*Initial template copy numbers, based on specimen Ct values, are reported for both real time methods. The standard curve for this analysis was generated with HPeV1 sRNA, using the TS Real-Time PCR method described in Example 3 ($r^2$ = 0.997). Virus isolation was attempted in Vero cells.

These results demonstrate that the methods disclosed herein can be used to detect all known species of Parechovirus including both the HPeVs and the LVs, and including novel parechoviruses, with a high degree of specificity and sensitivity. In addition, these methods have been shown to have the ability to amplify a wide variety of parechovirus isolates, from a variety of different clinical specimens.

Example 5

Primers for Determining which Parechovirus Species is Present

This example describes primers used in methods of determining which particular species of Parechovirus is present. Methods for using these primers are described in Example 6. Although particular examples of primers are provided, one skilled in the art will recognize that small modifications (such as variations in 1-2 nucleotides, for example 1-2 substitutions, deletions or additions) can be made to these sequences, without losing the ability to amplify parechovirus nucleic acid sequences.

```
cDNA primers
AN273
                                      (SEQ ID NO: 6)
5' AAR TAG TC 3'

AN274
                                      (SEQ ID NO: 7)
5' AAR TAA TC 3'

AN275
                                      (SEQ ID NO: 8)
5' TCR CAG TT 3'

AN276
                                      (SEQ ID NO: 9)
5' TCR CAA TT 3'

AN277
                                      (SEQ ID NO: 10)
5' ATR AAT TT 3'

AN278
                                      (SEQ ID NO: 11)
5' ATR AAC TT 3'

PCR 1 primers
AN180 forward:
                                      (SEQ ID NO: 12)
5' GAT AAT ACT TTT GAA ATG ACN ATH CCN TA 3'

AN80 reverse:
                                      (SEQ ID NO: 13)
5' CC ACC AAA TCT AAT GCC ATA ATG YTT RTA RAA NCC 3' snPCR 2 A and 2 B primers
seminested PCR 2 A
AN180
                                      (SEQ ID NO: 12)
5' GAT AAT ACT TTT GAA ATG ACN ATH CCN TA 3'

AN267 reverse
                                      (SEQ ID NO: 14)
5' GAA TAG TAG GGT GCA GAT AGN GWC ATY TGY TC 3' seminested PCR 2 B
AN280 forward
                                      (SEQ ID NO: 15)
5' GTA GAC AAC CTA TTT GGN MGN GCN TGG 3'

AN279
                                      (SEQ ID NO: 16)
5' TCT AAT GCC ATA ATG YTT RTA RAA NCC 3'

Nested PCR 2 primers
AN280 forward
                                      (SEQ ID NO: 15)
5' GTA GAC AAC CTA TTT GGN MGN GCN TGG 3'

AN267
                                      (SEQ ID NO: 14)
5' GAA TAG TAG GGT GCA GAT AGN GWC ATY TGY TC-3'
```

Variants of SEQ ID NOS: 6-16 can be generated and used in the methods described herein. For example, substitutions in the 5' non-degenerate portion can be made using methods known in the art.

Example 6

Identification of the Parechovirus Species

This example describes methods used to determine, once it is concluded that the sample contains parechovirus, which species of Parechovirus is present. The method generally includes sequencing at least a portion of the viral protein 1 (VP1) region of parechovirus (see FIG. 4). However, one skilled in the art will appreciate that minor variations to these methods will not alter the ability to sequence the VP1 region.

The specimens included cerebrospinal fluids (CSF) submitted to The Children's Hospital laboratory with surplus volume in 2005. Many CSFs were submitted for clinical investigation of febrile illness with a particular concern for central nervous system (CNS) disease or to rule out serious bacterial infection of newborns. Enterovirus (EV) 5' non-translated region (NTR) RT-PCR was positive for nine patients. RNA was extracted from the CSF samples using the method described in Example 2, and then analyzed for the presence of parechovirus using 5'NTR snRT-PCR as described in Example 3.

Samples testing positive for parechovirus were further analyzed to determine which Parechovirus species was present, using nested RT-PCR amplification of a portion of the viral protein 1 (VP1) gene. VP1 amplicons were sequenced to determine which Parechovirus species was present (such as HPeV1, HPeV2, HPeV3, LV, or an as yet unidentified parechovirus). The resulting VP1 sequences were compared to other parechovirus VP1 sequences from GenBank and from the CDC sequence database for molecular analyses. Additional testing for EV was performed using VP1 CODEHOP semi-nested RT-PCR (Nix et al., *J. Clin. Microbiol., in press,* 2006) for determining EV positive or negative results and the EV type by sequencing the VP1 amplicons.

For clinical CSF samples, RNA was extracted using the method described in Example 2, reverse transcribed, and the cDNA subjected to amplification. A second round of semi-nested PCR was performed. Table 7 shows a summary of the primer combinations, product sizes, and parechovirus group specificity:

TABLE 7

Primers used to identify Parechovirus species.

| Primer combination | PCR product size (bp)* | Group specificity |
| --- | --- | --- |
| cDNA (RT): SEQ ID NOS: 6-11 | Not applicable | HPeV and Ljungan |
| PCR 1: SEQ ID NOS: 12 and 13 | 994 | HPeV and Ljungan |
| snPCR 2A: SEQ ID NOS: 12 and 14 | 703 | HPeV and Ljungan |
| snPCR 2B: SEQ ID NOS: 15 and 16 | 575 | HPeV and Ljungan |
| Nested PCR: SEQ ID NOS: 15 and 14 | 292 | HPeV and Ljungan |

*These product sizes are relative to the genome of HPeV 1, Harris. Due to the variable nature of the VP1 gene (specifically insertions and deletions) the actual product sizes from other parechoviruses may vary slightly.

Reverse Transcription

Synthesis of cDNA was carried out in a 10 µl reaction containing 5 µl of RNA, 100 µM each dNTP (Amersham Biosciences, Piscataway, N.J.), 2 µl of 5× reaction buffer (Invitrogen, Carlsbad, Calif.), 0.01 M dithiothreitol (DTT), 0.5 pmol each cDNA primer (SEQ ID NOS: 6-11), 20 U of RNasin (Promega Corp., Madison, Wis.), and 100 U of Superscript II reverse transcriptase (Invitrogen). Following incubation at 22° C. for 10 minutes, 45° C. for 45 minutes, and 95° C. for 5 minutes, the entire 10 µl RT reaction was then used in the first PCR reaction (50 µl final volume).

Amplification

Following reverse transcription, the resulting cDNA was amplified. The PCR1 reaction composition included 5 µl of 10×PCR buffer (Roche Applied Science), 200 µM each dNTP, 50 pmol each of primers shown in SEQ ID NO: 12 and 13, and 2.5 U of Taq DNA polymerase (Roche Applied Science), which was amplified with 40 cycles of: 95° C. for 30 seconds, 42° C. for 30 seconds, and 60° C. for 45 seconds. This was followed by a 4° C. hold. This generated a PCR 1 reaction mixture that included amplicons that included the VP1 sequence.

After the first round of amplification, a second round of amplification was performed as follows. One microliter of the first PCR reaction was added to a second PCR reaction (PCR2A and 2B, Option 1; or PCR2, Option 2) for semi-nested or nested amplification. PCR2A contained 40 pmol each of primers shown in SEQ ID NOS: 12 and 14, 200 µM each dNTP, 5 µl of 10× FastStart Taq buffer (Roche Applied Science), and 2.5 U of FastStart Taq DNA polymerase (Roche Applied Science) in a final volume of 50 µl. The FastStart Taq polymerase was activated by incubation at 95° C. for 6 minutes prior to 40 amplification cycles of 95° C. for 30 seconds, 60° C. for 20 seconds, and 72° C. for 15 seconds. PCR2B contained 40 pmol each of primers shown in SEQ ID NOS: 15 and 16, 200 µM each dNTP, 5 µl of 10× FastStart Taq buffer (Roche Applied Science), and 2.5 U of FastStart Taq DNA polymerase (Roche Applied Science) in a final volume of 50 µl. The FastStart Taq polymerase was activated by incubation at 95° C. for 6 minutes prior to 40 amplification cycles of 95° C. for 30 seconds, 60° C. for 20 seconds, and 72° C. for 15 seconds. Nested PCR2 contained 40 pmol each of primers shown in SEQ ID NOS: 15 and 14, 200 µM each dNTP, 5 µl of 10× FastStart Taq buffer (Roche Applied Science), and 2.5 U of FastStart Taq DNA polymerase (Roche Applied Science) in a final volume of 50 µl. The FastStart Taq polymerase was activated by incubation at 95° C. for 6 minutes prior to 40 amplification cycles of 95° C. for 30 seconds, 60° C. for 20 seconds, and 72° C. for 15 seconds.

The second PCR (PCR2, 2A, and 2B) amplification conditions were: 95° C. for 10 minutes, followed by 45 cycles of 95° C. for 30 seconds, 50° C. for 30 seconds, and 72° C. for 60 seconds. This was followed by a 72° C. for 5 minutes, then a 4° C. hold. The nested PCR amplification conditions were: 95° C. for 10 minutes, followed by 45 cycles of 95° C. for 30 seconds, 50° C. for 20 seconds, and 72° C. for 30 seconds. This was followed by a 72° C. for 5 minutes, then a 4° C. hold. The snPCR 2A and 2B reactions resulted in the amplification of full-length VP1, while the nested VP1 reaction amplified a portion of VP1 (see FIG. 4).

Purification and Sequencing of Amplicons

The amplicons from the second amplification reaction (either snPCR 2A, snPCR 2B, or nested PCR 2) were purified using gel electrophoresis. After separating the products resulting from the second amplification on a 1.2% agarose horizontal slab gel using 1× LB buffer, the appropriate bands were excised from the gel using the Qiaquick Gel Extraction Kit (cat. #28706; Qiagen) according to the manufacturer's instructions. If weak bands were present and cut from the gel, the purified PCR product was dried in a dessicator to concentrate the DNA. The purified amplicons were reconstituted into 15 to 20 µl water, and stored at −20° C. or at 4° C.

The purified amplicons were sequenced using the ABI PRISM BigDye 3.0 protocol for PCR products and 1 μl of a 10 μM stock of the primers shown in SEQ ID NOS: 12-16 for the corresponding template. The sequencing reactions were purified with Centri-Sep 8 strips (cat. # CS-912; Princeton Separations), according to the manufacturer's protocol, dried, and resuspended in 20 μl formamide. The sequencing reactions were analyzed on the ABI Prism 3100 Genetic Analyzer, according to the manufacturer's instructions.

Results

Using these methods above, 13/243 (5.3%) CSF specimens were 5' NTR positive for parechovirus. The 13 parechovirus positive specimens were confirmed with VP1 nested RT-PCR. Analysis of the VP1 amplicon sequences identified all 13 viruses as HPeV3. Screening for the presence of EV found 14/243 (5.7%) CSF specimens were positive for EV. Serotypes included E6, E7, E18, EV71, CVA9, CVB2, and CVB3.

Clinical data was available for 12/13 HPeV3-infected patients. All of the HPeV3 infected infants were full term infants; 7 males and 6 females. The average age (26.4 days; n=12) of the HPeV3 positive neonates is significantly younger than the average age (17.3 yrs; n=12) of the EV infected group (p≦0.014; Wilcoxon two sample test). All of the infants were less than or equal to 7 weeks in age and all were admitted to rule out serious bacterial infection. Fever, fussiness, decreased appetite, and rash were the most commonly reported signs and symptoms. Most of the rashes started on the lower extremities and in two cases were confined there. Only one patient in this series had abnormally high numbers of WBCs identified in the CSF and that patient had a traumatic lumbar puncture. There were 2500 WBCs/mm3 and 729,000 RBCs/mm3. A repeat lumbar puncture was done but was not successful. Two patients had elevated proteins in the CSF. Both of these patients had traumatic lumbar punctures (one was the previously described patient). One patient had a CSF protein of 2400 mg/dL with 729,000 RBCs/mm3; the other had a CSF protein of 417 mg/dL with 8388 RBCs/mm3. All of the HPeV3 positive infants had CSF submitted for bacterial culture and EV PCR and all were negative for those studies. Eleven of thirteen infants had herpes simplex virus (HSV) PCR performed on CSF and all were negative. C-reactive protein was performed on five infants and all were normal.

Colorado HPeV3 VP1 amino acid sequences are very closely related to HPeV3s identified previously in the US, Bolivia, Canada, Japan, and the Netherlands. Amino-acid identity (Distances, Wisconsin Sequence Analysis Package) for the HPeV3 cluster ranged from 96.2-100% in the VP1 window analyzed, which represents one-third of the complete HPeV3 VP1 protein. Nucleic acid identity for the same HPeV3 cluster and VP1 window ranged from 94-100%. In addition to Colorado, HPeV3 was identified in CA, GA, KS, TN, TX, WI, and WY (no clinical data available) in 2005.

Figure 5:
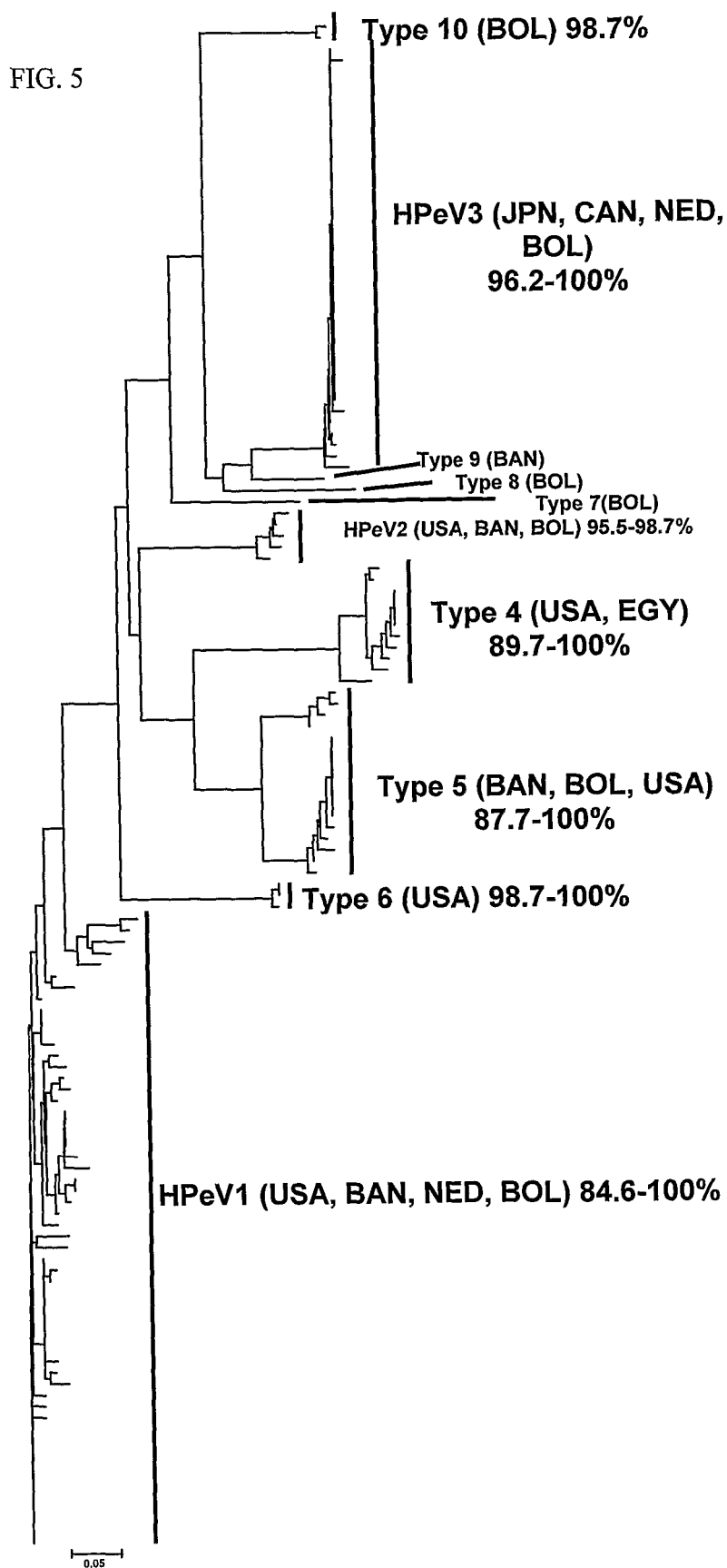
FIG. 5 is an unrooted neighbor-joining tree (CLUSTAL X, v1.83) of HPeV partial viral protein 1 (VP1) sequences. HPeV 1, 2, 3, and seven additional types identified are shown. The numbers are percent amino-acid identity within each type, determined with Distances (Wisconsin Sequence Analysis Package). Prototype strains are shown in italics. Country abbreviations are: BAN=Bangladesh, BOL=Bolivia, CAN=Canada, EGY=Egypt, JPN=Japan, NET=Netherlands, and USA=United States.

The data indicate that an outbreak of HPeV3 disease occurred in the study area in 2005. In addition, the data indicate that the disclosed methods can be used to detect parechovirus from a variety of specimens, and to identify new parechovirus (FIG. 5). For example, in addition to amplifying and detecting HPeV1-3, seven potential new HPeV serotypes (provisionally called HPeV4-10; see FIG. 5) have been identified.

Example 7

Detection and Identification of Parechovirus Obtained from a Subject

This example describes methods to determine if a subject is infected with any known species of Parechovirus, for example by determining if a sample obtained from a subject contains parechovirus nucleic acid molecules, and if so, which parechovirus is present.

RNA extracted from a sample obtained from the subject having or suspected of being infected with parechovirus is reversed transcribed into cDNA. Ideally, the sample is one which would contain parechovirus if the subject were infected with parechovirus. Methods of obtaining such samples are known in the art. Exemplary samples include lung or spleen tissue, CSF, stool samples, rectal swabs, and nasopharyngeal swabs. RNA can be extracted from the sample using methods known in the art, for example using a commercially available kit. In addition, cDNA can be reverse transcribed from the RNA using a commercially available kit.

At least a portion of the 5'NTR is amplified from the cDNA (such as a region within nucleotides 293-681, see FIG. 1A-C), and in some examples quantitated. In some examples, the production of cDNA from RNA and amplification of the cDNA is performed in a single reaction vessel. In other examples, the cDNA is produced in one reaction vessel, and then amplified in another reaction vessel (for example the cDNA may be stored for a period of time then amplified at a later time). If desired, multiple amplification reactions can be performed, for example to increase the sensitivity of the assay. In a particular example, the snPCR method described in Example 3 is used.

If the results indicate parechovirus is present in the sample, the particular species of parechovirus present can be determined, for example by sequencing at least a portion of VP1. However, if desired, this step can be performed independently of first determining if parechovirus is present in the sample. For example, the nested PCR method described in Example 6 can be used to amplify a region of VP1. The resulting amplicon sequence is compared to a database containing known parechovirus VP1 sequences. If the amplicon nucleic acid sequence and the database VP1 sequence share greater than 75% sequence identity (such as at least 80%, at least 85%, at least 90%, or even at least 95% sequence identity), or share greater than 85% amino acid sequence identity (such as at least 90%, or even at least 95% sequence identity), they are the same type. For example, if the amplicon nucleotide sequence has 90% identity to HPeV2, then it is concluded that the sample (and the subject from whom the sample was obtained) is infected with HPeV2. If the amplicon nucleic acid sequence and the database VP1 sequence share less than 70% sequence identity but more than 45% identity, this indicates that the species is a "new" or previously unidentified (or unsequenced) Parechovirus species. If the amplicon nucleic acid sequence and the database VP1 sequence share 70-75% sequence identity, the typing result is indeterminant.

In view of the many possible embodiments to which the principles of the disclosed invention may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A method of detecting a human parechovirus (HPeV) and Ljungan virus (LV) species of Parechovirus, comprising,
   contacting cDNA reverse transcribed from RNA isolated from a sample with a composition that permits amplification of the cDNA, wherein the composition comprises a forward primer and a first reverse primer, wherein the forward and first reverse primers hybridize to opposite strands of a Parechovirus 5' nontranslated region (5'NTR), and wherein the forward primer comprises a degenerate oligonucleotide comprising at least 95% sequence identity to the nucleic acid sequence set forth as SEQ ID NO: 1, and wherein the first reverse primer comprises a degenerate oligonucleotide comprising at least 95% sequence identity to the nucleic acid sequence set forth as SEQ ID NO: 2 or SEQ ID NO: 4;
   performing an amplification procedure under conditions sufficient to amplify Parechovirus cDNA and produce a Parechovirus amplicon Parechovirus, wherein the Parechovirus amplicon comprises at least a portion of the Parechovirus 5'NTR nucleic acid sequence if Parechovirus is present in the sample, thereby generating a first reaction sample; and
   detecting whether the Parechovirus amplicon is present in the first reaction sample, wherein the presence of the Parechovirus amplicon indicates that at least one HPeV or LV species of Parechovirus is present in the sample.

2. The method of claim 1, wherein the human parechovirus species of Parechovirus comprises human parechovirus genotype 1 (HPeV1), HPeV2, or HPeV3.

3. The method of claim 1, wherein the amplification procedure comprises a polymerase chain reaction (PCR).

4. The method of claim 1, wherein the first reverse primer comprises a degenerate oligonucleotide comprising at least 95% sequence identity to the nucleic acid sequence set forth as SEQ ID NO: 4.

5. The method of claim 4, further comprising performing a second amplification procedure prior to detecting whether the Parechovirus amplicon is present in the first reaction sample, wherein the second amplification procedure comprises:
   amplifying at least a portion of the first reaction sample with a composition comprising the forward primer and a second reverse primer, wherein the second reverse primer hybridizes to the Parechovirus 5'NTR upstream of where the first reverse primer hybridizes to the Parechovirus 5'NTR, and wherein the second reverse primer comprises a degenerate oligonucleotide comprising at least 95% sequence identity to the nucleic acid sequence set forth as SEQ ID NO: 2, under conditions sufficient to amplify Parechovirus cDNA, thereby producing a second reaction sample comprising a second Parechovirus amplicon.

6. The method of claim 5, wherein the detection is performed using gel electrophoresis and visualization of amplicons contained in a resulting gel, size separation matrix, capillary electrophoresis and detection of the emerging amplicons, probing for the presence of the Parechovirus amplicons using a probe, or sequencing the Parechovirus amplicons.

7. The method of claim 1, wherein the composition further comprises a probe comprising a degenerate oligonucleotide comprising at least 95% sequence identity to the nucleic acid sequence set forth as SEQ ID NO: 3, and wherein the probe comprises a fluorophore and a quencher molecule.

8. The method of claim 7, wherein detection comprises detection of fluorescence from the fluorophore, wherein the presence of detectable fluorescence indicates that Parechovirus amplicons are present and that the sample contains Parechovirus, and wherein the absence of detectable fluorescence indicates that Parechovirus amplicons are not present and that the sample does not contain Parechovirus.

9. The method of claim 1, wherein the Parechovirus is not isolated from a cell culture prior to isolating RNA from the sample.

10. The method of claim 1, wherein the method has a sensitivity of at least 95%.

11. The method of claim 1, wherein the method has a specificity of at least 95%.

12. The method of claim 1, further comprising quantitating the Parechovirus amplicon.

13. The method of claim 1, wherein if the Parechovirus amplicon is detected, further comprising determining which Parechovirus species is present in the sample.

14. The method of claim 13, wherein determining which Parechovirus species is present comprises:
   sequencing at least a portion of the viral protein 1 (VP1) gene of Parechovirus, thereby obtaining a VP1 sequence; and
   determining which Parechovirus species is present by comparing the VP1 sequence to a sequence database containing Parechovirus VP1 sequences, wherein sequencing at least a portion of the VP1 gene of Parechovirus comprises:

contacting cDNA reverse transcribed from RNA isolated from a sample with a composition that permits amplification of the cDNA, wherein the composition comprises a second forward primer and a third reverse primer, wherein the second forward and third reverse primers hybridize to opposite strands of a Parechovirus VP1 region, and wherein the second forward primer comprises a degenerate oligonucleotide comprising at least 95% sequence identity to the nucleic acid sequence set forth as SEQ ID NO: 12 or SEQ ID NO: 15, and wherein the third reverse primer comprises a degenerate oligonucleotide comprising at least 95% sequence identity to the nucleic acid sequence set forth as SEQ ID NO: 13, SEQ ID NO: 14, or SEQ ID NO: 16;

performing an amplification procedure under conditions sufficient to amplify Parechovirus cDNA and produce a Parechovirus amplicon from Parechovirus, wherein the Parechovirus amplicon comprises at least a portion of the Parechovirus VP1 nucleic acid sequence if Parechovirus is present in the sample, thereby generating a second reaction sample;

amplifying at least a portion of the second reaction sample under conditions sufficient to amplify Parechovirus cDNA and produce a Parechovirus amplicon from Parechovirus, in a composition comprising a third forward primer and a fourth reverse primer, wherein the third forward primer and the fourth reverse primer hybridize to the Parechovirus VP1 gene within the VP1 region amplified by the second forward and third reverse primers, thereby generating a third reaction sample; and sequencing the third reaction sample.

15. The method of claim 14, wherein the second forward primer comprises a degenerate oligonucleotide comprising at least 95% sequence identity to the nucleic acid sequence set forth as SEQ ID NO: 12 and the third reverse primer comprises a degenerate oligonucleotide comprising at least 95% sequence identity to the nucleic acid sequence set forth as SEQ ID NO: 13.

16. The method of claim 14, wherein the second forward primer comprises a degenerate oligonucleotide comprising at least 95% sequence identity to the nucleic acid sequence set forth as SEQ ID NO: 15 and the third reverse primer comprises a degenerate oligonucleotide comprising at least 95% sequence identity to the nucleic acid sequence set forth as SEQ ID NO: 16.

17. The method of claim 14, wherein the third forward primer comprises a degenerate oligonucleotide comprising at least 95% sequence identity to the nucleic acid sequence set forth as SEQ ID NO: 15 and the fourth reverse primer comprises a degenerate oligonucleotide comprising at least 95% sequence identity to the nucleic acid sequence set forth as SEQ ID NO: 14.

18. The method of claim 1, wherein the sample is a whole blood or a fraction thereof, a bronchial wash, cerebrospinal fluid, an eye swab, a conjunctival swab, a swab or scraping from a lesion, a nasopharyngeal swab, an oral or buccal swab, pericardial fluid, a rectal swab, serum, sputum, saliva, stool, a stool extract, a throat swab, urine, brain tissue, heart tissue, intestinal tissue, kidney tissue, liver tissue, lung tissue, pancreas tissue, spinal cord tissue, skin tissue, spleen tissue, thymus tissue, cells from a tissue culture, a supernatant from a tissue culture, or tissue from an experimentally infected animal.

19. A method of identifying which Parechovirus species is present in a sample, comprising:

contacting cDNA reverse transcribed from RNA isolated from the sample with a composition that permits amplification of the cDNA, wherein the composition comprises a first forward primer and a first reverse primer, wherein the first forward primer hybridizes to a Parechovirus VP3 region, wherein the first forward primer comprises a degenerate oligonucleotide comprising at least 95% sequence identity to the nucleic acid sequence set forth as SEQ ID NO: 12, and wherein the first reverse primer hybridizes to a Parechovirus 2A region, wherein the first reverse primer comprises a degenerate oligonucleotide comprising at least 95% sequence identity to the nucleic acid sequence set forth as SEQ ID NO: 13;

performing an amplification procedure under conditions sufficient to amplify Parechovirus cDNA and produce a Parechovirus amplicon, wherein the Parechovirus amplicon comprises at least a portion of the Parechovirus VP1 nucleic acid sequence if Parechovirus is present in the sample, thereby generating a first reaction sample;

amplifying at least a portion of the first reaction sample under conditions sufficient to amplify Parechovirus cDNA and produce a Parechovirus amplicon, in a composition comprising a second forward primer and a second reverse primer, wherein the second forward and reverse primers permit amplification of at least a portion of Parechovirus VP1 region, thereby generating a second reaction sample; and sequencing amplicons present in the second reaction sample, thereby generating an amplicon sequence, wherein the amplicon sequence permits a determination of which Parechovirus species is present in the sample.

20. The method of claim 19, further comprising comparing the amplicon sequence to a sequence database containing Parechovirus VP1 sequences.

21. A degenerate oligonucleotide consisting of any of SEQ ID NOS: 1-4 or 6-16.

22. A kit comprising:
at least two of the degenerate oligonucleotides of claim 21.

23. The kit of claim 22, further comprising one or more agents for PCR or reverse transcription.

24. A degenerate oligonucleotide comprising at least 95% sequence identity to SEQ ID NO: 2, wherein the degenerate oligonucleotide retains the ability to hybridize to a Parechovirus 5'NTR sequence under very high stringency conditions.

25. The degenerate oligonucleotide of claim 24, wherein the degenerate oligonucleotide comprises SEQ ID NO: 2.

26. A degenerate oligonucleotide comprising at least 95% sequence identity to any of SEQ ID NOS: 6-16, wherein the degenerate oligonucleotide retains the ability to hybridize to a Parechovirus VP1 nucleic acid sequence under very high stringency conditions.

27. The degenerate oligonucleotide of claim 26, wherein the degenerate oligonucleotide comprises any of SEQ ID NOS: 6-16.

28. A degenerate oligonucleotide comprising at least 95% sequence identity to any of SEQ ID NOS: 1, 3 or 4.

29. The degenerate oligonucleotide of claim 28, comprising SEQ ID NO: 1, 3 or 4.

* * * * *